(12) United States Patent
Arcot Desai et al.

(10) Patent No.: US 12,333,443 B2
(45) Date of Patent: Jun. 17, 2025

(54) SYSTEMS AND METHODS FOR USING FEDERATED LEARNING FOR TRAINING CENTRALIZED SEIZURE DETECTION AND PREDICTION MODELS ON DECENTRALIZED DATASETS

(71) Applicant: NeuroPace, Inc., Mountain View, CA (US)

(72) Inventors: Sharanya Arcot Desai, Sunnyvale, CA (US); Thomas K. Tcheng, Pleasant Hill, CA (US)

(73) Assignee: NeuroPace, Inc, Mountain View, CA (US)

( * ) Notice: Subject to any disclaimer, the term of this patent is extended or adjusted under 35 U.S.C. 154(b) by 1030 days.

(21) Appl. No.: 17/356,342

(22) Filed: Jun. 23, 2021

(65) Prior Publication Data

US 2021/0407678 A1    Dec. 30, 2021

Related U.S. Application Data

(60) Provisional application No. 63/043,514, filed on Jun. 24, 2020.

(51) Int. Cl.
*G06N 3/09* (2023.01)
*G06F 8/65* (2018.01)
(Continued)

(52) U.S. Cl.
CPC .............. *G06N 3/098* (2023.01); *G06F 8/65* (2013.01); *G16H 50/20* (2018.01)

(58) Field of Classification Search
CPC .......... G16H 50/20; G16H 20/30; G06N 3/04; G06N 3/088; G06N 3/098; G06F 8/65
See application file for complete search history.

(56) References Cited

U.S. PATENT DOCUMENTS 6,016,449 A    1/2000   Fischell et al.
6,480,743 B1   11/2002  Kirkpatrick et al.
(Continued)

FOREIGN PATENT DOCUMENTS

WO    2016154298    9/2016

OTHER PUBLICATIONS

Hard, A., Federated Learning for Mobile Keyboard Prediction, Retrieved from Internet:<https://arxiv.org/abs/1811.03604> (Year: 2019).*

(Continued)

*Primary Examiner* — Paul M Knight
*Assistant Examiner* — Bart I Rylander
(74) *Attorney, Agent, or Firm* — LOZA & LOZA, LLP; David S. Sarisky

(57) ABSTRACT

A server for updating a current version of a machine learning model resident in implanted medical devices includes an interface, a memory, and a processor. The interface is configured to receive a plurality of updated versions of the machine learning model from a plurality of remote sources remote from the server. The remote source may be, e.g., implanted medical devices and/or subservers. The processor is coupled to the memory and the interface and is configured to aggregate the plurality of updated versions to derive a server-updated version of the machine learning model, and to transmit the server-updated version of the machine learning model to one or more of the plurality of remote sources as a replacement for the current version of the machine learning model.

29 Claims, 18 Drawing Sheets

(51) Int. Cl.
    *G06N 3/098*    (2023.01)
    *G16H 50/20*    (2018.01)

(56) References Cited

U.S. PATENT DOCUMENTS

| | | | |
|---|---|---|---|
| 6,594,524 | B2 | 7/2003 | Esteller et al. |
| 6,810,285 | B2 | 10/2004 | Pless et al. |
| 7,209,787 | B2 | 4/2007 | Dilorenzo |
| 7,231,254 | B2 | 6/2007 | Dilorenzo |
| 7,242,984 | B2 | 7/2007 | Dilorenzo |
| 7,277,758 | B2 | 10/2007 | Dilorenzo |
| 7,280,867 | B2 | 10/2007 | Frei et al. |
| 7,324,851 | B1 | 1/2008 | Dilorenzo |
| 7,403,820 | B2 | 7/2008 | Dilorenzo |
| 7,529,582 | B1 | 5/2009 | Dilorenzo |
| 7,542,803 | B2 | 6/2009 | Heruth et al. |
| 7,599,736 | B2 | 10/2009 | Dilorenzo |
| 7,623,928 | B2 | 11/2009 | Dilorenzo |
| 7,676,273 | B2 | 3/2010 | Goetz et al. |
| 7,747,325 | B2 | 6/2010 | Dilorenzo |
| 7,822,481 | B2 | 10/2010 | Gerber et al. |
| 7,853,322 | B2 | 12/2010 | Bourget et al. |
| 7,853,329 | B2 | 12/2010 | Dilorenzo |
| 7,894,903 | B2 | 2/2011 | John |
| 7,899,545 | B2 | 3/2011 | John |
| 7,930,035 | B2 | 4/2011 | Dilorenzo |
| 7,957,797 | B2 | 6/2011 | Bourget et al. |
| 7,957,809 | B2 | 6/2011 | Bourget et al. |
| 7,966,073 | B2 | 6/2011 | Pless et al. |
| 7,974,696 | B1 | 7/2011 | Dilorenzo |
| 8,027,730 | B2 | 9/2011 | John |
| 8,126,567 | B2 | 2/2012 | Gerber et al. |
| 8,543,214 | B2 | 9/2013 | Osorio et al. |
| 8,543,217 | B2 | 9/2013 | Stone et al. |
| 8,694,115 | B2 | 4/2014 | Goetz et al. |
| 8,706,237 | B2 | 4/2014 | Giftakis et al. |
| 8,731,656 | B2 | 5/2014 | Bourget et al. |
| 8,903,486 | B2 | 12/2014 | Bourget et al. |
| 9,931,508 | B2 | 4/2018 | Burdick et al. |
| 9,955,921 | B2 | 5/2018 | Esteller et al. |
| 10,123,717 | B2 | 11/2018 | Tcheng |
| 10,252,056 | B2 | 4/2019 | Mogul |
| 10,729,907 | B2 | 8/2020 | Desai et al. |
| 2003/0018367 | A1 | 1/2003 | Dilorenzo |
| 2003/0171789 | A1 | 9/2003 | Malek et al. |
| 2004/0199217 | A1 | 10/2004 | Lee et al. |
| 2004/0199218 | A1 | 10/2004 | Lee et al. |
| 2004/0215286 | A1 | 10/2004 | Stypulkowski |
| 2004/0267330 | A1 | 12/2004 | Lee et al. |
| 2005/0021103 | A1 | 1/2005 | Dilorenzo |
| 2005/0021104 | A1 | 1/2005 | Dilorenzo |
| 2005/0060007 | A1 | 3/2005 | Goetz |
| 2005/0060008 | A1 | 3/2005 | Goetz |
| 2006/0265022 | A1 | 11/2006 | John et al. |
| 2007/0073355 | A1 | 3/2007 | Dilorenzo |
| 2007/0142862 | A1 | 6/2007 | Dilorenzo |
| 2007/0142874 | A1 | 6/2007 | John |
| 2007/0162086 | A1 | 7/2007 | Dilorenzo |
| 2007/0167991 | A1 | 7/2007 | Dilorenzo |
| 2007/0208212 | A1 | 9/2007 | Dilorenzo |
| 2007/0287931 | A1 | 12/2007 | Dilorenzo |
| 2008/0058773 | A1 | 3/2008 | John |
| 2008/0061961 | A1 | 3/2008 | John |
| 2008/0071314 | A1 | 3/2008 | John |
| 2008/0109005 | A1 | 5/2008 | Trudeau et al. |
| 2008/0119900 | A1 | 5/2008 | Dilorenzo |
| 2009/0018609 | A1 | 1/2009 | Dilorenzo |
| 2010/0023089 | A1 | 1/2010 | Dilorenzo |
| 2010/0217348 | A1 | 8/2010 | Dilorenzo |
| 2010/0241183 | A1 | 9/2010 | Dilorenzo |
| 2010/0249859 | A1 | 9/2010 | Dilorenzo |
| 2011/0040353 | A1 | 2/2011 | Gerber et al. |
| 2011/0307030 | A1 | 12/2011 | John |
| 2016/0228705 | A1 | 8/2016 | Crowder et al. |
| 2019/0117978 | A1 | 4/2019 | Desai et al. |
| 2020/0272857 | A1 | 8/2020 | Desai et al. |

OTHER PUBLICATIONS

Dumpelmann, M., Early seizure detection for closed loop direct neurostimulation devices in epilepsy, Retrieved from Internet:<https://iopscience.iop.org/article/10.1088/1741-2552/ab094a/meta> (Year: 2019).*

Smith, V., et al, Federated Multi-Task Learning, Retrieved from Internet:<https://proceedings.neurips.cc/paper/2017/hash/6211080fa89981f66b1a0c9d55c61d0f-Abstract.html> (Year: 2017).*

Brown, J., Identification of novel DNA repair proteins via primary sequence, secondary structure, and homology, Retrieved from Internet:<https://link.springer.com/article/10.1186/1471-2105-10-25> (Year: 2009).*

Camara, et al, Resting tremor classification and detection in Parkinson's disease patients, Retrieved from Internet:<https://www.sciencedirect.com/science/article/pii/S1746809414001414> (Year: 2015).*

Eirich, T., Beam: A Tool for Flexible Software Update, Retrieved from Internet:<https://scholar.google.com/scholar?cluster=2104970323893850914&hl=en&as_sdt=0,47> (Year: 1994).*

Kusonmano, et al, Effects of Pooling Samples on the Performance of Classification Algorithms: A Comparative Study, Retrieved from Internet:<https://onlinelibrary.wiley.com/doi/full/10.1100/2012/278352> (Year: 2012).*

McMahan, et al, Communication-Efficient Learning of Deep Networks from Decentralized Data, Retrieved from Internet:<https://proceedings.mlr.press/v54/mcmahan17a?ref=https://githubhelp.com> (Year: 2017).*

Thalij, et al, Multiobjective Glowworm Swarm Optimization-Based Dynamic Replication Algorithm for Real-Time Distributed Databases, Retrieved from Internet:<https://onlinelibrary.wiley.com/doi/full/10.1155/2018/2724692> (Year: 2018).*

Wang, et al, Federated Learning with Matched Averaging, Retrieved from Internet:<https://arxiv.org/abs/2002.06440> (Year: 2020).*

Baud et al., "Multi-day rhythms modulate seizure risk in epilepsy." Nat Commun 9, 88, (2018).

Brinkmann et al., "Forecasting Seizures Using Intracranial EEG Measures and SVM in Naturally Occurring Canine Epilepsy," G. A. PLoS.One.,10:e0133900 (2015).

Cantero et al., "Sleep-dependent theta oscillations in the human hippocampus and neocortex,", J Neurosci,23:10897-10903 (2003).

Carrington et al.,"Effect of focal low-frequency stimulation on amygdala-kindled afterdischarge thresholds and seizure profiles in fast- and slow-kindling rat strains," Epilepsia, 48:1604-1613 (2007).

Chan et al., "Automated seizure onset detection for accurate onset time determination in intracranial EEG," Clin. Neurophysiol., 119:2687-2696 (2008).

Colom, "Septal networks: relevance to theta rhythm, epilepsy and Alzheimer's disease," J Neurochem., 96:609-623 (2006).

Crespel et al., "Sleep influence on seizures and epilepsy effects on sleep in partial frontal and temporal lobe epilepsies," M. Clin. Neurophysiol.,111 Suppl 2:S54-S59 (2000).

Desai et al., "Quantitative electrocorticographic biomarkers of clinical outcomes in mesial temporal lobe epileptic patients treated with the RNS system", Clinical Neurophysiology 130, 1364-1374, (2019).

García-Hernández et al., "Septo-hippocampal networks in chronic epilepsy", EAT Neurol. Mar. 2010; 222(1):86-92.

Goodman et al., "Preemptive low-frequency stimulation decreases the incidence of amygdala-kindled seizures," Epilepsia,46:1-7 (2005).

Herman et al., "Distribution of partial seizures during the sleep-wake cycle: differences by seizure onset site," Neurology,56:1453-1459 (2001).

Karoly et al., "The circadian profile of epilepsy improves seizure forecasting." Brain 140, 2169-2182, (2017).

Karoly et al., "Forecasting cycles of seizure likelihood". Epilepsia 61, 776-786, (Dec. 19, 2019).

Kisilev et al., "Medical Image Description Using Multi-task-loss CNN." Deep Learning and Data Labeling for Medical Applications. DLMIA Labels 2016 2016. Lecture Notes in Computer Science(), vol. 10008. Springer, Cham. https://doi.org/10.1007/978-3-319-46976-8_13.

(56) References Cited

OTHER PUBLICATIONS

Litt et al., "Epileptic Seizures May Begin Hours in Advance of Clinical Onset: A Report of Five Patients", Neuron, vol. 30, 51-64, Apr. 2001.
Logesparan et al., "Optimal features for online seizure detection", Medical & Biological Engineering & Computing, 50.7 (2012): 659-669, and Supplementary Material relating to article.
Lysyansky et al., "Optimal No. of stimulation contacts for coordinated reset neuromodulation," Front Neuroeng.,6:5 (2013).
Malow, "The interaction between sleep and epilepsy," Epilepsia,48 Suppl 9:36-38 (2007).
Maturana et al., "Critical slowing down as a biomarker for seizure susceptibility". Nat Commun 11, 2172, (2020).
Meisel et al., "Intrinsic excitability measures track antiepileptic drug action and uncover increasing/ decreasing excitability over the wake/sleep cycle". Proc Natl Acad Sci U S A 112, 14694-14699, (Nov. 6, 2015).
Miller et al., "Anticonvulsant effects of the experimental induction of hippocampal theta activity," Epilepsy Res., 18:195-204 (1994).
Minecan et al., "Relationship of epileptic seizures to sleep stage and sleep depth," Sleep,25:899-904 (2002).
Ng et al., "Why are seizures rare in rapid eye movement sleep? Review of the frequency of seizures in different sleep stages," M. Epilepsy Res.Treat.,2013:932790 (2013).
Ogren et al., "Three-dimensional hippocampal atrophy maps distinguish two common temporal lobe seizure-onset patterns," Epilepsia, 50(6):1361-1370 (2009).
Osorio et al., "Real-Time Automated Detection and Quantitative Analysis of Seizures and Short-Term Prediction of Clinical Onset", Epilepsia, 39(6):615-627 (1998).
Perucca et al., "Intracranial electroencephalographic seizure-onset patterns: effect of underlying pathology," J. Brain: 137:183-196 (2014).
Popovych et al., "Desynchronizing electrical and sensory coordinated reset neuromodulation", Frontiers in Human Neuroscience, Mar. 20, 2012, vol. 6, Article 58.
Quigg et al., Electrocorticographic events from long-term ambulatory brain recordings can potentially supplement seizure diaries. Epilepsy Res 161, 106302, (2020).
Schiller et al., "Characterization and comparison of local onset and remote propagated electrographic seizures recorded with intracranial electrodes," Epilepsia,39:380-388 (1998).
Skarpaas et al., "Clinical and electrocorticographic response to antiepileptic drugs in patients treated with responsive stimulation", Epilepsy & Behavior 83, 192-200, (2018).
Tass et al., "Long-lasting desynchronization in rat hippocampal slice induced by coordinated reset stimulation", Physical Review F 80, 011902 (2009).
Tass et al., "Coordinated reset has sustained aftereffects in Parkinsonian monkeys," Ann.Neurol,72:816-820 (2012).
Uriguen et al., "Comparison of background EEG activity of different groups of patients with idiopathic epilepsy using Shannon spectral entropy and cluster-based permutation statistical testing". PLoS One 12, (Sep. 18, 2017).
Van Putten et al., "Detecting temporal lobe seizures from scalp EEG recordings: a comparison of various features," Clin. Neurophysiol.,116:2480-2489 (2005).
Vaswani et al., "Attention is all you need". Advances in Neural Information Processing Systems 30 (2017).
Wackermann, "Beyond mapping: estimating complexity of multichannel EEG recordings," Acta Neurobiol.Exp.(Wars.),56:197-208 (1996).
Welsh et al., "A circadian rhythm of hippocampal theta activity in the mouse," Physiol.Behav,35:533-538 (1985).
Zeiler et al., "Visualizing and Understanding Convolutional Networks", ArXiv:1311.2901v3, Nov. 28, 2013, pp. 1-11.
Ali Hossam Shoeb, and John Guttag: "Application of Machine Learning to Epileptic Seizure Detection", Appearing in the Proceedings of the 27th International Conference on Machine Learning, Haifa, Israel 2010, Copyright 2010.
Spencer, S. S., Guimaraes, P., Katz, A., Kim, J., and Spencer, D. Epilepsia: "Morphological patterns of seizures recorded intracranially," 33:537-545 (1992).
Lee, S. A., Spencer, D. D., and Spencer, S. S. Epilepsia: "Intracranial EEG seizure-onset patterns in neocortical epilepsy," 41:297-307 (2000).
Langan, Y., Nashef, L., and Sander, J. W.: "Case-control study of SUDEP," Neurology,64:1131-1133 (2005).
Bateman, L. M., Li, C. S., Lin, T. C., and Seyal, M. Epilepsia: "Serotonin reuptake inhibitors are associated with reduced severity of ictal hypoxemia in medically refractory partial epilepsy," 51:2211-2214 (2010).
Ali Hossam Shoeb: Thesis "Application of Machine Learning to Epileptic Seizure Onset Detection and Treatment", Submitted to Harvard-MIT Div. of Health Sciences re Dr. of Philosophy in EE and Med Engineering at MIT, Sep. 2009.
Maryann D'Alessandro, George Vachtsevanos, Rosana Esteller, Javier Echauz, Stephen Cranstoun, Greg Worrell, Landi Parish and Brian Litt: "A multi-feature and multi-channel univariate selection process for seizure prediction", Clinical Neurophysiology 116 (2005) 506-516.
Isa Conradsen, Student Member; IEEE, Sándor Beniczky, Karsten Hoppe, Peter Wolf and Helge B. D. Sorensen Member, IEEE: "Automated algorithm for generalised tonic-clonic epileptic seizure onset detection based on sEMG zero-crossing rate", IEEE Transactions on Biomedical Engineering, Copyright IEEE 2011, pubs-permissions@ieee.org.
Alaa Kharbouch, Ali Shoeb, John Guttag, and Sydney S. Cash: "An algorithm for seizure onset detection using intracranial EEG," Epilepsy Balmy. Dec. 2011; 22(01): S29-S35.
Yusuf U Khan, Omar Farooq and Priyanka Sharma: "Automatic Detection of Seizure Onset in Pediatric EEG", International Journal of Embedded Systems and Applications (IJESA) vol. 2, No. 3, Sep. 2012.
Yizhuo Zhang, Guanghua Xu, Jing Wang, Lin Liang: "An automatic patient-specific seizure onset detection method in intracranial EEG based on incremental nonlinear dimensionality reduction, Computers in Biology and Medicine 40 (2010) 889-899. Automated Detection and Quantitative Analysis of Seizures and Short-Term Prediction of Clinical Onset", Epilepsia, 39(6):615-627 (1998).
A.J. Gabor, R.R. Leach, and F.U. Dowla: "Automated Seizure Detection Using a Self-Organizing Neural Network", Dept. of Neurology, University of CA, Davis Medical Center, Jan. 5, 1996; Published Apr. 15, 1996, Electroencephalography and Clinical Neurophysiology 99 (1996) 257-266.
A.J. Gabor: "Automated Seizure Detection Using a Self-Organizing Neural Network, Validation and Comparison with Other Detection Strategies", Dept. of Neurology, University of CA, Davis Medical Center, Accepted for Publication Feb. 28, 1998, Electroencephalography and Clinical Neurophysiology 107 (1998) 27-32.
Russakovsky et al., "ImageNet Large Scale Visual Recognition Challenge", International Journal of Computer Vision, available online Apr. 11, 2015, published Dec. 2015; vol. 115, Issue 3, DOI 10.1007/s11263-015-0816-; pp. 211-252.
Lecun et al., "Deep Learning", Nature, May 27, 2015, vol. 521; DOI:10.1038/nature14539; pp. 436-444.
Xu et al., "Survey of Clustering Algorithms", IEEE Transactions on Neural Networks, vol. 16, No. 3, May 1, 2005; 35 pages.
Krizhevsky et al., "ImageNet Classification with Deep Convolutional Neural Networks", NIPS'12 Proceedings of the 25th International Conference on Neural Information Processing Systems—vol. 1, pp. 1097-1105, Dec. 3, 2012.
Desai, Sharanya, "Insights from mining large-scale human EcoG data", ICTAL2017, The Penumbra Conference, presented Aug. 21, 2017; 9 pages.
Esteva et al. "Dermatologist level classification of skin cancer with deep neural networks", Nature, vol. 542, published Feb. 2, 2017, pp. 115-118.
Desai et al., "Transfer-learning for differentiating epileptic patients who respond to treatment based on chronic ambulatory ECoG data," in 2019 9th International IEEE/EMBS Conference on Neural Engineering (NER), 2019: IEEE, pp. 1-4.

(56) References Cited

OTHER PUBLICATIONS

Hussein, Ramy et al. "Epileptic Seizure Detection: A Deep Learning Approach", ArXiv:1803.09848v1, Mar. 27, 2018, pp. 1-12; 2018.

Tsiouris, Kostas M. et al. "A Long Short-Term Memory deep learning network for the prediction of epileptic seizures using EEG signals", Computers in Biology and Medicine, vol. 99, Aug. 1, 2018, pp. 24-37.

Thodoroff, M. et al. "Learning Robust Features using Deep Learning for Automatic Seizure Detection", ArXiv:1608.00220, Jul. 31, 2016, pp. 1-12.

Pailla, Tejaswy et al. "Autoencoders for learning template spectrograms in electrocorticographic signals", Journal of Neural Engineering, vol. 16, No. 1, Jan. 14, 2019.

Ling, Zhen-Huia et al. "Waveform Modeling and Generation Using Hierarchical Recurrent Neural Networks for Speech Bandwidth Extension", IEEE/ACM Transactions on Audio, Speech, and Language Processing, vol. 26, No. 5, pp. 883-894, May 2018.

Zeiler, Matthew D. et al. "Visualizing and Understanding Convolutional Networks", ArXiv:1311.2901v3, Nov. 28, 2013, pp. 1-11.

\* cited by examiner

Base Model (602) Weights

|    | a1  | a2  | a3  |
|----|-----|-----|-----|
| b1 | 0.7 | 0.1 | 0.3 |
| b2 | 0.6 | 0.5 | 0.2 |
| b3 | 0.4 | 0.9 | 0.1 |

|    | b1  | b2  | c3  |
|----|-----|-----|-----|
| c1 | 0.8 | 0.5 | 0.6 |
| c2 | 0.9 | 0.1 | 0.7 |

Round 1 subserver-updated model (608) weights

From Hospital A

|    | a1   | a2   | a3   |
|----|------|------|------|
| b1 | 0.75 | 0.12 | 0.31 |
| b2 | 0.62 | 0.54 | 0.22 |
| b3 | 0.41 | 0.92 | 0.11 |

|    | b1   | b2   | c3   |
|----|------|------|------|
| c1 | 0.82 | 0.56 | 0.63 |
| c2 | 0.91 | 0.1  | 0.75 |

From Hospital C

|    | a1   | a2   | a3   |
|----|------|------|------|
| b1 | 0.65 | 0.15 | 0.90 |
| b2 | 0.54 | 0.65 | 0.21 |
| b3 | 0.32 | 0.80 | 0.16 |

|    | b1   | b2   | c3   |
|----|------|------|------|
| c1 | 0.65 | 0.43 | 0.66 |
| c2 | 0.43 | 0.15 | 0.74 |

From Hospital D

|    | a1   | a2   | a3   |
|----|------|------|------|
| b1 | 0.73 | 0.15 | 0.33 |
| b2 | 0.61 | 0.53 | 0.22 |
| b3 | 0.43 | 0.96 | 0.11 |

|    | b1   | b2   | c3   |
|----|------|------|------|
| c1 | 0.85 | 0.55 | 0.65 |
| c2 | 0.94 | 0.13 | 0.73 |

From Hospital E

|    | a1   | a2   | a3   |
|----|------|------|------|
| b1 | 0.72 | 0.08 | 0.23 |
| b2 | 0.61 | 0.42 | 0.11 |
| b3 | 0.48 | 0.92 | 0.24 |

|    | b1   | b2   | c3   |
|----|------|------|------|
| c1 | 0.84 | 0.52 | 0.61 |
| c2 | 0.99 | 0.15 | 0.75 |

Round 1 Server-updated model (610) weights

|    | a1     | a2    | a3     |
|----|--------|-------|--------|
| b1 | 0.7125 | 0.125 | 0.435  |
| b2 | 0.595  | 0.535 | 0.185  |
| b3 | 0.41   | 0.9   | 0.1525 |

|    | b1     | b2     | b3     |
|----|--------|--------|--------|
| c1 | 0.79   | 0.515  | 0.6375 |
| c2 | 0.8175 | 0.1325 | 0.7425 |

FIG. 7

SYSTEMS AND METHODS FOR USING FEDERATED LEARNING FOR TRAINING CENTRALIZED SEIZURE DETECTION AND PREDICTION MODELS ON DECENTRALIZED DATASETS

CROSS-REFERENCE TO RELATED APPLICATION(S)

This application claims the benefit of and priority to U.S. Provisional Patent Application Ser. No. 63/043,514, filed Jun. 24, 2020, for "Systems and Methods for Using Federated Learning for Training Centralized Seizure Detection and Prediction Models on Decentralized Datasets," the entire disclosure of which is incorporated herein by reference.

TECHNICAL FIELD

The present disclosure relates generally to systems and methods for training machine learning models, and more particularly, to systems and methods that use federated learning to train centralized seizure detection and prediction models on decentralized datasets.

BACKGROUND

Implantable neurostimulation systems, such as the RNS System manufactured by NeuroPace, Inc., are capable of recording electrocorticographic (ECoG) activity through chronically implanted electrodes. See, e.g., Bergey, G. K., et al. (2015). "Long-term treatment with responsive brain stimulation in adults with refractory partial seizures." Neurology 84(8): 810-817, and Connolly, A. T., et al. (2015). "Local field potential recordings in a non-human primate model of Parkinsons disease using the Activa PC+S neurostimulator." J Neural Eng 12(6): 066012.

In the case of epilepsy for example, continuous or semi-continuous ECoG data may contain periods of baseline (e.g., no seizures) activity, periods of pre-ictal activity (e.g., activity captured within the hours before the onset of seizures) and ictal activity (e.g., seizures). See, e.g., Karoly, P. J., et al. (2016). "Interictal spikes and epileptic seizures: their relationship and underlying rhythmicity." Brain 139(Pt 4): 1066-1078. Reliable seizure detection (i.e., detection of the ictal periods in the ECoG data) and seizure prediction (i.e., detection of the pre-ictal periods in the ECoG data) algorithms will undoubtedly improve quality of life for epilepsy patients. See, Ramgopal, S., et al. (2014). "Seizure detection, seizure prediction, and closed-loop warning systems in epilepsy." Epilepsy Behav 37: 291-307.

Several machine and deep learning based analyses have shown that seizure detection and prediction are possible, but these analyses are usually performed on small datasets (i.e., either data from individual patients or small groups of patients). See, e.g., Ramgopal, S., et al. (2014). "Seizure detection, seizure prediction, and closed-loop warning systems in epilepsy." Epilepsy Behav 37: 291-307, Gadhoumi, K., et al. (2016). "Seizure prediction for therapeutic devices: A review." J Neurosci Methods 260: 270-282, and Baldassano, S. N., et al. (2017). "Crowdsourcing seizure detection: algorithm development and validation on human implanted device recordings." Brain 140(6): 1680-1691.

Since machine and deep learning models learn trends from data, the amount of data used for training usually determines the performance of these models, with models trained on large datasets almost always outperforming models trained on smaller datasets. Additionally, training models on data from multiple patients may also make the models more generalizable which is desirable. See, e.g., LeCun, Y., et al. (2015). "Deep learning." Nature 521(7553): 436-444. "Generalizable" in this context means that the trained models may be readily applied on other, e.g., new or newer, patients for whom only a limited dataset may be available.

Traditionally, large datasets used for machine learning models and deep learning models are stored in one central location such as an on-premises or cloud-based data server that is managed by an entity, e.g., a university or a private company, which trains machine and deep learning models on the large datasets. For example, if a private company is interested in training an algorithm for self-driving cars, the company would collect training data, store it in a central on-premises or cloud-based data server and train a machine/deep learning model on this data.

In the domain of healthcare, sending patient data from a patient's implanted device or from an external storage server that is owned or controlled by the patient, or from the patient's hospital-controlled servers, which can be on-premises or cloud-based, to a central location that is managed by a university or private company for storage and analysis purposes may not always be feasible for several reasons. For example, storing the same data in multiple locations, such as in a patient-specific device and a central location, and/or storing all patient data in one central location may increase the risk of unwanted data exposure. Also, patients or hospitals may not be willing to share their raw data. Raw data refers to data that are in the original data format, as acquired and stored by a patient's implanted device. For example, raw data may be an EEG signal sensed from the patient and stored in digital format in an EEG record in the implanted device. Raw data may also be data that results from the processing of other data by the implanted device. For example, as described in detail later in this disclosure, an implanted device may be configured to process EEG signals to obtain other types of data, such as detections of specified electrographic events, or counts of occurrences of specified electrographic events, or measures of the duration of electrographic events, or the rate of occurrences of electrographic events. These types of data are stored in the implanted device and are considered raw data.

Accordingly, in the healthcare industry the use of machine learning may be limited to patient-specific instances. For example, in some implanted neurostimulation systems, current machine learning and deep learning based seizure detection and prediction models are trained with data from the patient in whom the system is implanted. Such training may not be ideal or efficient because a large amount of data is required to be collected from the patient before the seizure detection and prediction model can be trained and applied to the patient's data. Furthermore, seizure detection and prediction models that are trained on a single patient's data do not generalize well to other, e.g. new or newer, patients.

In more recent years, large datasets are becoming increasingly available in the healthcare sector enabling the training of deep learning models directly from data. However, some of these patients or the hospitals caring for these patients may be unwilling to share their raw data with an external entity due to data privacy and/or data security concerns. Thus, these large datasets remain unavailable for the training of deep learning based seizure detection and prediction models.

It is therefore desirable to enable the training of a machine learning model used in implanted medical devices in a way that involves the use of raw (or derived) datasets stored across a large number of such devices without requiring direct sharing of the raw data by these devices.

SUMMARY

The present disclosure relates to a method of updating a current version of a machine learning model resident in implanted medical devices. The method may be performed by a server in conjunction with a plurality of implanted medical devices and further in conjunction with one or more subservers. The method includes receiving a plurality of updated versions of the machine learning model from a plurality of remote sources remote from the server. The remote sources may be implanted medical devices (IMD) that provide IMD-updated versions of the machine learning model to the server, and/or subservers that provide sub-server-updated versions of the machine learning model to the server. The method also includes aggregating the plurality of updated versions to derive a server-updated version of the machine learning model. The method further includes, transmitting the server-updated version of the machine learning model to one or more of the plurality of remote sources as a replacement for the current version of the machine learning model.

The present disclosure also relates to a server for updating a current version of a machine learning model resident in implanted medical devices. The server includes an interface, a memory, and a processor. The interface is configured to receive a plurality of updated versions of the machine learning model from a plurality of remote sources remote from the server. The remote source may be implanted medical devices that provide IMD-updated versions of the machine learning model to the server, and/or subservers that provide subserver-updated versions of the machine learning model to the server. The processor of the server is coupled to the memory and the interface and is configured to aggregate the plurality of updated versions of the machine learning model to derive a server-updated version of the machine learning model. The processor is also configured to transmit via the interface, the server-updated version of the machine learning model to one or more of the plurality of remote sources as a replacement for the current version of the machine learning model.

The present disclosure also relates to a subserver for updating a current version of a machine learning model resident in implanted medical devices. The subserver includes an interface, a memory, and a processor. The interface is configured to receive a plurality of IMD-updated versions of the machine learning model from a plurality of implanted medical devices. The processor is coupled to the memory and the interface and is configured to aggregate the plurality of IMD-updated versions of the machine learning model to derive a subserver-updated version of the machine learning model. The processor is also configured to transmit via the interface, the subserver-updated version of the machine learning model to server for further processing derivation of a server-updated version of the machine learning model.

The present disclosure also relates to an implantable medical device including an interface, a memory storing a dataset, and a processor. The in interface configured to provide to a server, an IMD-updated version of a current version of a machine learning model stored in the implantable medical device. The processor is coupled to the memory and the interface and is configured to generate the IMD-updated version of the machine learning model based on the dataset.

BRIEF DESCRIPTION OF THE DRAWINGS

Various aspects of apparatuses and methods will now be presented in the detailed description by way of example, and not by way of limitation, with reference to the accompanying drawings, wherein:

FIG. 7 are illustrations of example weights for the model of FIG. 5 that result from a model update process in accordance with the second scenario shown in FIGS. 6A and 6B.

DETAILED DESCRIPTION

Figure 1:
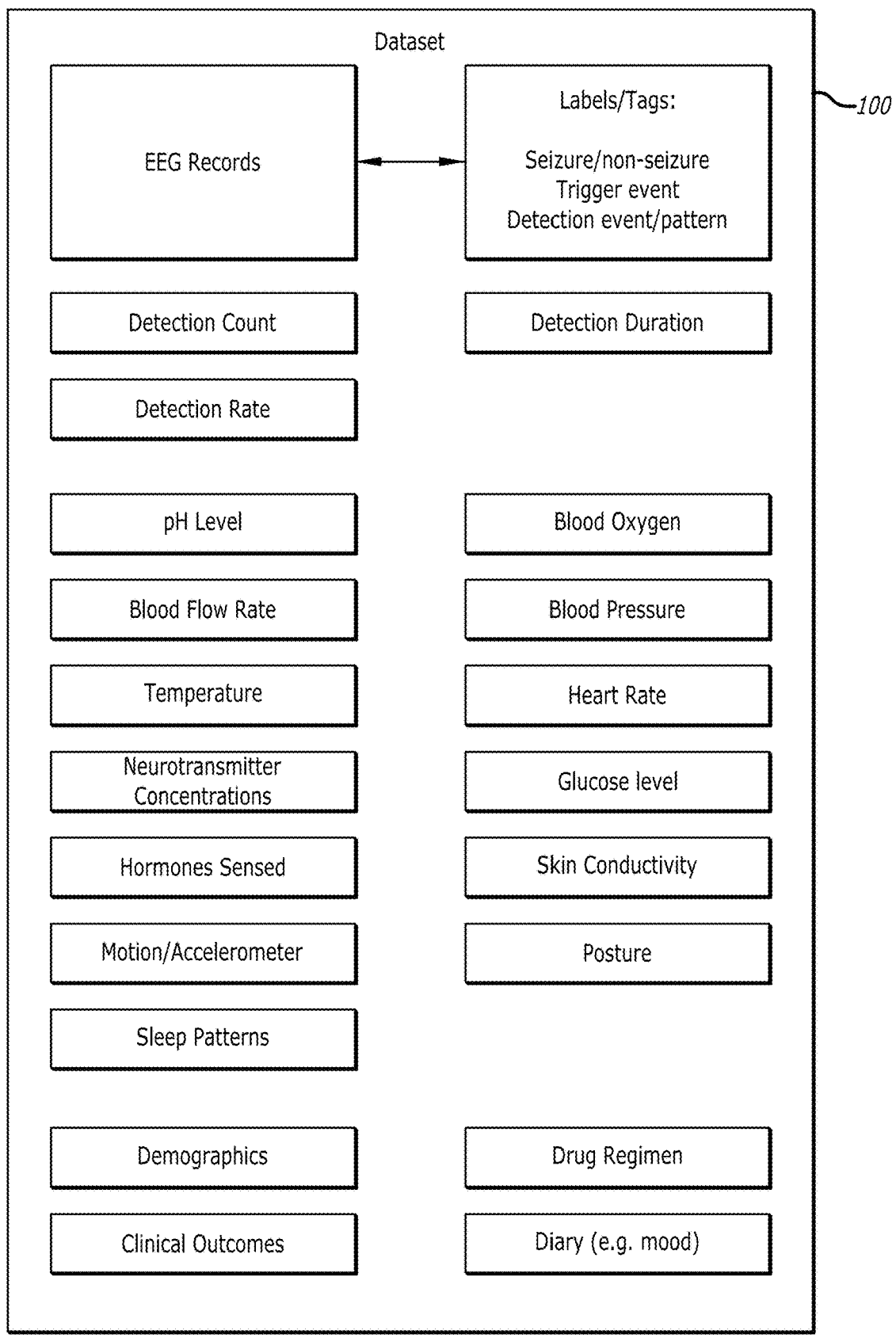
FIG. 1 is an illustration of different types of data that may be included in a dataset of an implanted neurostimulation system.

Disclosed herein are methods and systems that enable the updating of a machine learning model resident in a plurality of implanted medical devices, at a central server remote from the plurality of implanted medical devices and without central server reception of or access to raw data stored in the devices. The implanted medical devices may be, for example, neurostimulation systems that sense electrical brain activity, detect neurological events in accordance with a set of detection parameters, deliver electrical neurostimulation to the brain in accordance with a set of stimulation parameters, and store records of electrical brain activity. The machine learning model may be resident in the neurostimulation systems and may be used to detect neurological events, such as epileptic seizures or seizure onsets, from electrographic information.

In one embodiment of the methods and systems, current versions of the machine learning model resident in a number of implanted medical devices are periodically retrained locally at each device based on a dataset stored in that device. The retrained versions of the machine learning model generated by the implanted medical devices are transmitted to the central server and aggregated to generate a server-updated version of the machine learning model. The server-updated version of the machine learning model is then transmitted to the implanted medical devices as a replacement for the current version of the model.

In another configuration, the retrained versions of the machine learning model generated by the implanted medical devices are transmitted to one or more intermediate subservers between the central server and the implanted medical devices. Each subserver aggregates the retrained versions of the machine learning model it receives to generate a subserver-updated version of the machine learning model. The subserver-updated version of the machine learning model generated by each of the subservers is transmitted to the central server and aggregated to generate a server-updated version of the machine learning model. The server-updated version of the machine learning model is then transmitted to the implanted medical devices as a replacement for the current version of the model.

In another embodiment of the methods and systems, current versions of the machine learning model resident in a number of implanted medical devices are periodically retrained at a subserver remote from the implanted medical devices. To this end, one or more of the implanted medical devices periodically transmits its dataset to the subserver. The subserver may pool the datasets together to create a dataset, referred to herein as a "dataset pool," upon which it retrains the machine learning algorithm to generate a subserver-updated version of the machine learning model. Alternatively, the subserver may individually retrain the machine learning model of each implanted medical device on the dataset of that respective device, and then aggregate these individual machine learning models to generate a subserver-updated version of the machine learning model. In either case, the subserver-updated version of the machine learning model generated by each of the subservers is transmitted to the central server and aggregated to generate a server-updated version of the machine learning model. The server-updated version of the machine learning model is then transmitted to the implanted medical devices as a replacement for the current version of the model.

The disclosed training system employs federated or distributed learning to enable the training and updating of a machine learning model across numerous sets of training data without the need for centralizing the training data. See, e.g., Brisimi, T. S., et al. (2018). "Federated learning of predictive models from federated Electronic Health Records." Int J Med Inform 112: 59-67. Instead, locally-trained machine learning model instances are trained by the implanted medical devices themselves on training data stored in the devices. These locally-trained machine learning model instances are shared with a central server that aggregates the locally-trained machine learning model instances into a centrally-trained machine learning model. Accordingly, while the centrally-trained machine learning model is indirectly derived from data from many different implanted medical devices, the training data itself does not have to be transferred from the patients' devices to a central server, thus reducing the risk of unintended data exposures. Because the models are trained based on data from many different patients, the models may generalize well to other, e.g., new or newer, patients.

It should be noted that raw training data cannot be derived by the central server or a subserver from the shared, locally-trained machine learning models. It should be further noted that while the system is described as training a machine learning model, the machine learning model encompasses deep learning models.

Datasets

With reference to FIG. 1, as used herein, a "dataset" 100 refers to a collection of information or types of data that may be used to train, test, validate, and use a machine learning model. A dataset 100 may include one or more records or files of information from a patient in whom an implantable medical device is implanted. This information may include physiological information from the patient and non-physiological information related to the patient's environment, device configuration, device operation, demographics, conditions and therapies.

With respect to physiological information, in the case of an implanted neurostimulation system, a dataset 100 may include records or files of physiological information corresponding to electrical activity of the brain that is sensed by the system. Hereinafter, electrical activity of the brain is referred to as "EEG", and a physiological record corresponding to electrical activity of a patient's brain is referred to as an "EEG record." It will be understood that EEG includes electrical activity sensed directly from the neural tissue, which sometimes is referred to as electrocorticographic activity, an electrocorticogram, or "ECoG".

Figure 2A:
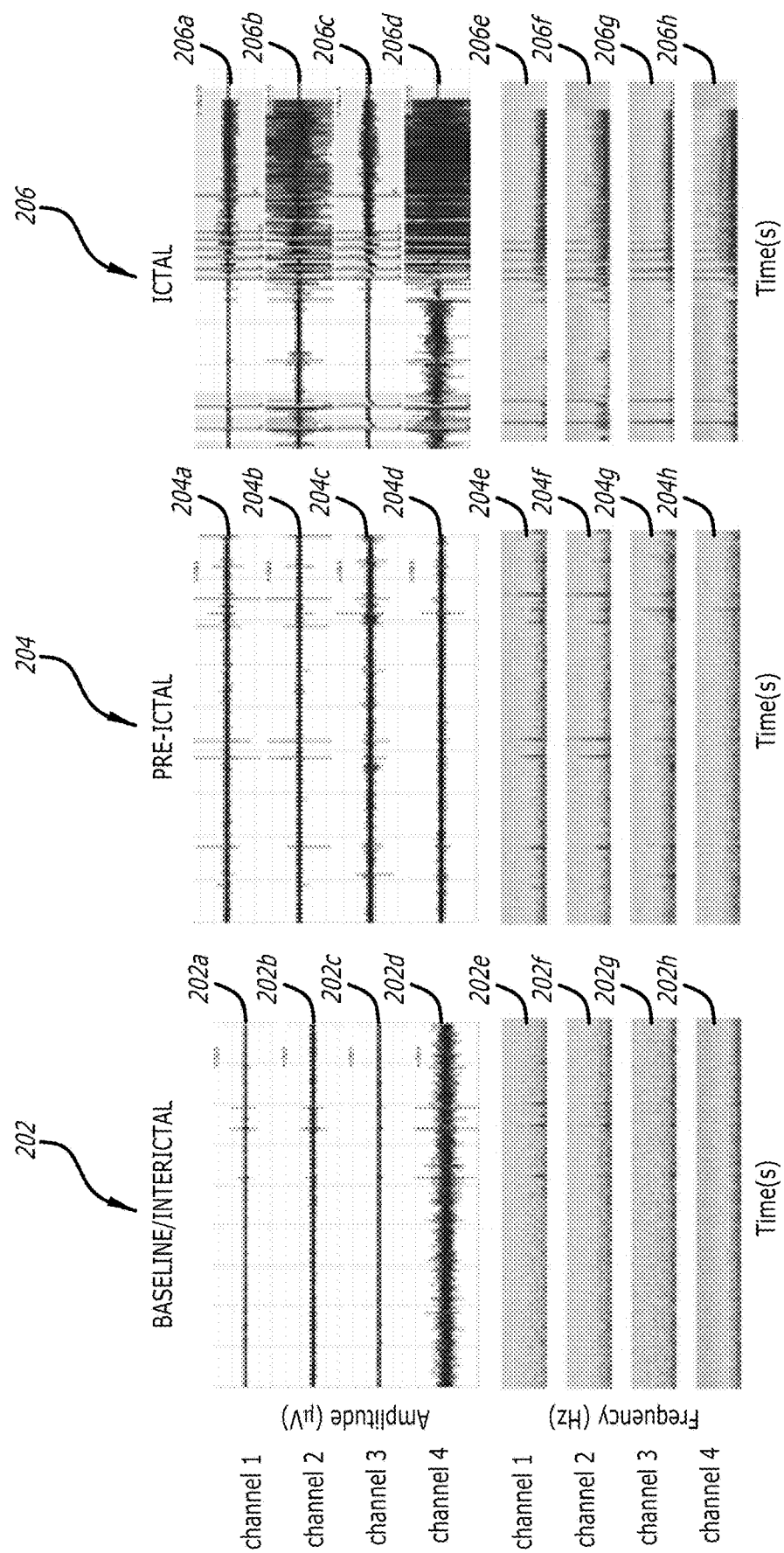
FIG. 2A are example time-series waveform visual representations of EEG records included in a dataset of an implanted neurostimulation system, and correspond to electrical activity of the brain as recorded by the implanted neurostimulation system, together with their corresponding spectrogram visual representations.

With additional reference to FIG. 2A, EEG records 202, 204, 206 included in a dataset 100 may be visualized or represented in different forms. In the upper portion of FIG. 2A, EEG records 202, 204, 206 are represented by time series waveform images 202a-d, 204a-d, 206a-d for each of four sensing channels of an implanted neurostimulation system. Each EEG record 202, 204, 206 was captured with an implanted neurostimulator system during a respective one of a baseline/interictal brain state (e.g., no seizure), a preictal brain state (e.g., activity captured within the hours before the onset of seizures), and an ictal brain states (e.g., a seizure) in an example patient. In the lower portion, the same EEG records 202, 204, 206 are represented by spectrograms 202e-h, 204e-h, 206e-h for each of four sensing channels.

Figure 2B:
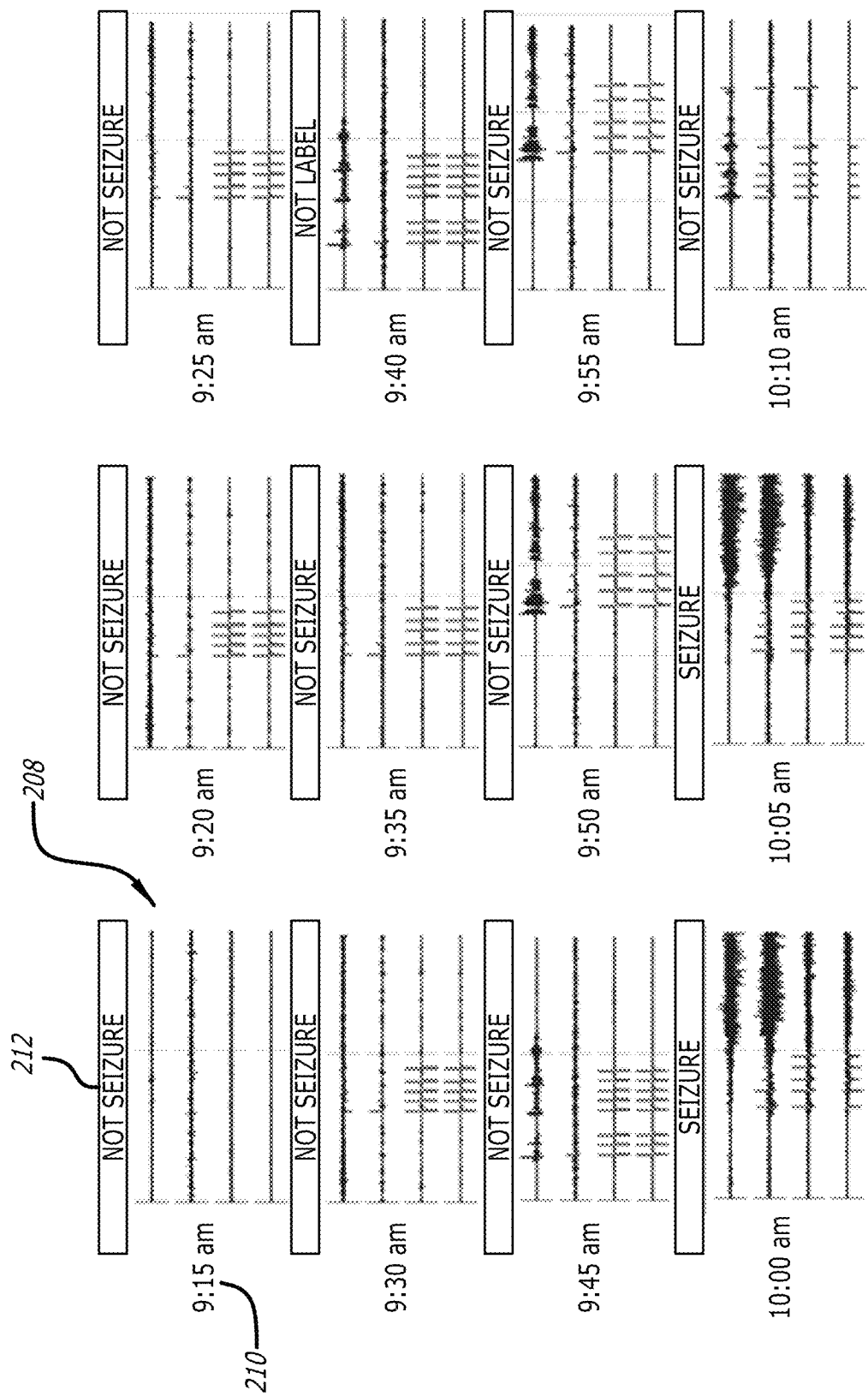
FIG. 2B are examples time-series waveform visual representations of EEG records included in a dataset of an implanted neurostimulation system, together with additional information, e.g., time stamps and seizure/non-seizure labels, associated with the records and included in the dataset.

With reference to FIG. 2B, additional information may be associated with EEG records. For example, each individual EEG record 208 may have an associated time stamp 210 corresponding to the time the EEG signals within the record were captured by the implanted neurostimulation system. Each individual EEG record 208 may also have an associated label 212 classifying the EEG signals within the record as being indicative of a seizure or not a seizure. Other examples of additional information that may be associated with each EEG record include the event that triggered creation of the EEG record. As described further below, such triggering events may include a detection of abnormal electrical activity in an EEG signal, a patient initiated event, e.g., a swipe of a magnet in the area of the implanted neurostimulation system, or a scheduled passage of time.

Figure 2C:
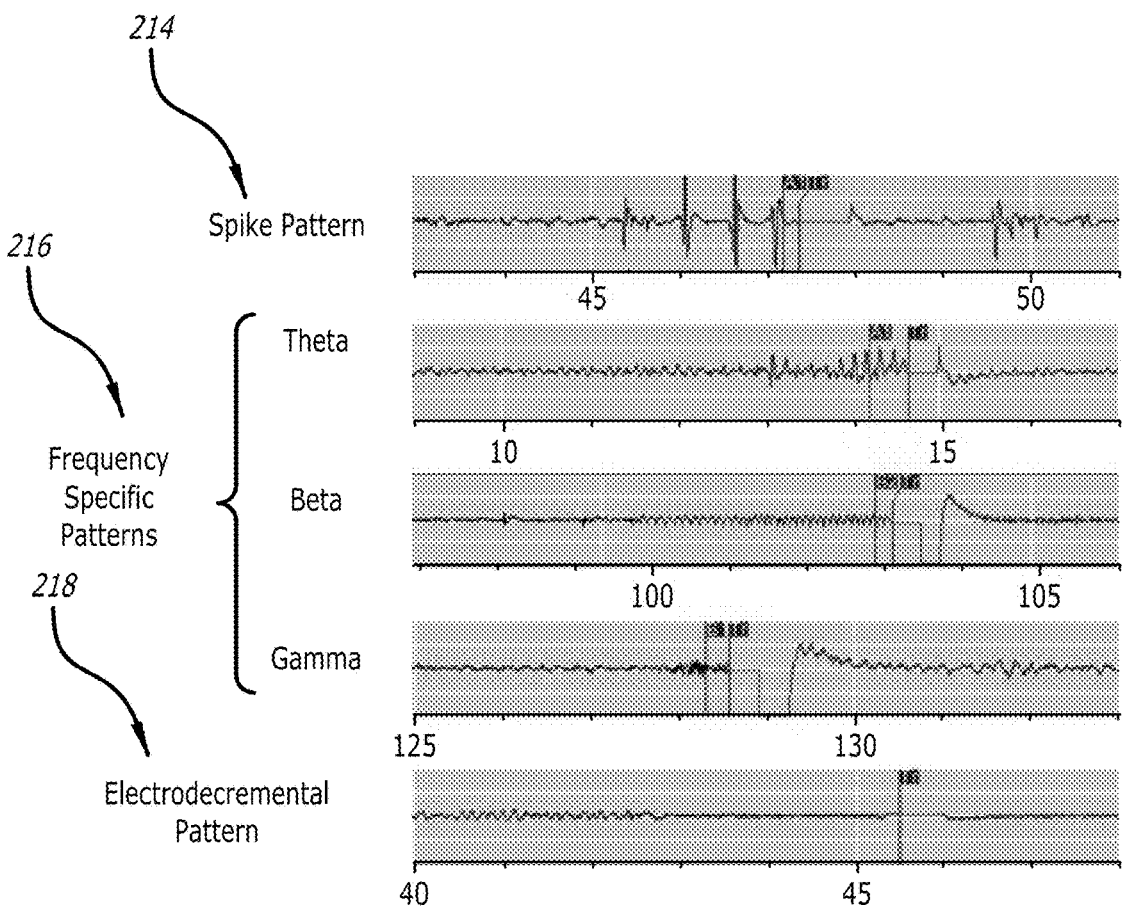
FIG. 2C are examples of time-series waveform visual representations of EEG records corresponding to patterns of electrical brain activity including spikes, oscillatory patterns, and amplitude and/or frequency changes.
Figure 2C:
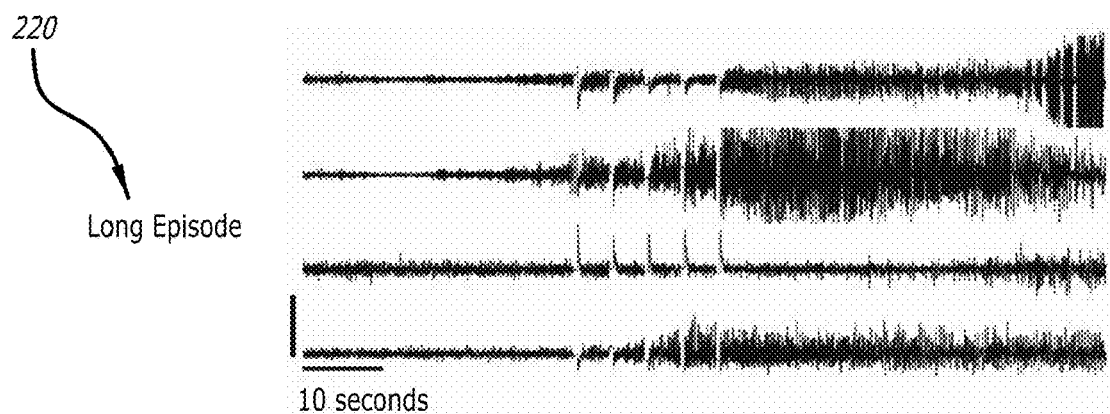

With reference to FIG. 1, additional information may be derived by an implanted neurostimulation system from sensed EEG signals and included in a dataset 100. For example, the implanted neurostimulation system may be configured to detect patterns in a patient's electrical brain activity and to maintain records of the timing of detections, the count of the number of detections, and a detection rate. The count of such detections may be included in a dataset 100, either with or without an EEG record of the detected patterns. With reference to FIG. 2C, example patterns of electrical brain activity include spikes 214, oscillatory patterns 216, and amplitude and/or frequency changes 218. The implanted neurostimulation system may also be configured to detect abnormal electrical brain activity having a duration that exceeds a specified threshold, and to maintain records of the timing and count of the number of such detections together with information, e.g., time stamps, indicative of the time and duration each detection. This abnormal electrical brain activity is referred to as a "long episode." An example pattern of a long episode 220 is shown in FIG. 2C. The count of detections of long episodes 220 and the respective duration information of each may be included in a dataset 100, either with or without EEG records of the detected long episodes.

While the methods and systems disclosed herein are primarily described with reference to EEG records, it will be appreciated that other physiological information and non-physiological information may be processed. To this end and with reference to FIG. 1, other types or modalities of physiological information may be included in a dataset 100. For example, physiological records may include measurements of pH level in neural tissue, blood oxygen levels in neural tissue, blood flow rates, neurotransmitters concentrations in neural tissue, temperatures, heart rates, blood pressures, blood glucose levels, hormones sensed in sweat, skin conductivity, accelerometer/motion recordings, posture, and sleep patterns. This information may be sensed and recorded locally by an implanted medical device, or sensed remote from the implanted medical device, such as from an external wearable device, and may be transmitted to the implanted device for local storage.

With respect to non-physiological information, a dataset 100 may include records or files of the patient's demographics (e.g., age, gender), the patient's drug regimen (e.g., type of drug, dose, and time of day of dose), and the patient's clinical outcomes, such as the rate of clinical seizures (e.g., as reported in a seizure diary), mood, or questionnaire information.

Overview of Training System

Figure 3:
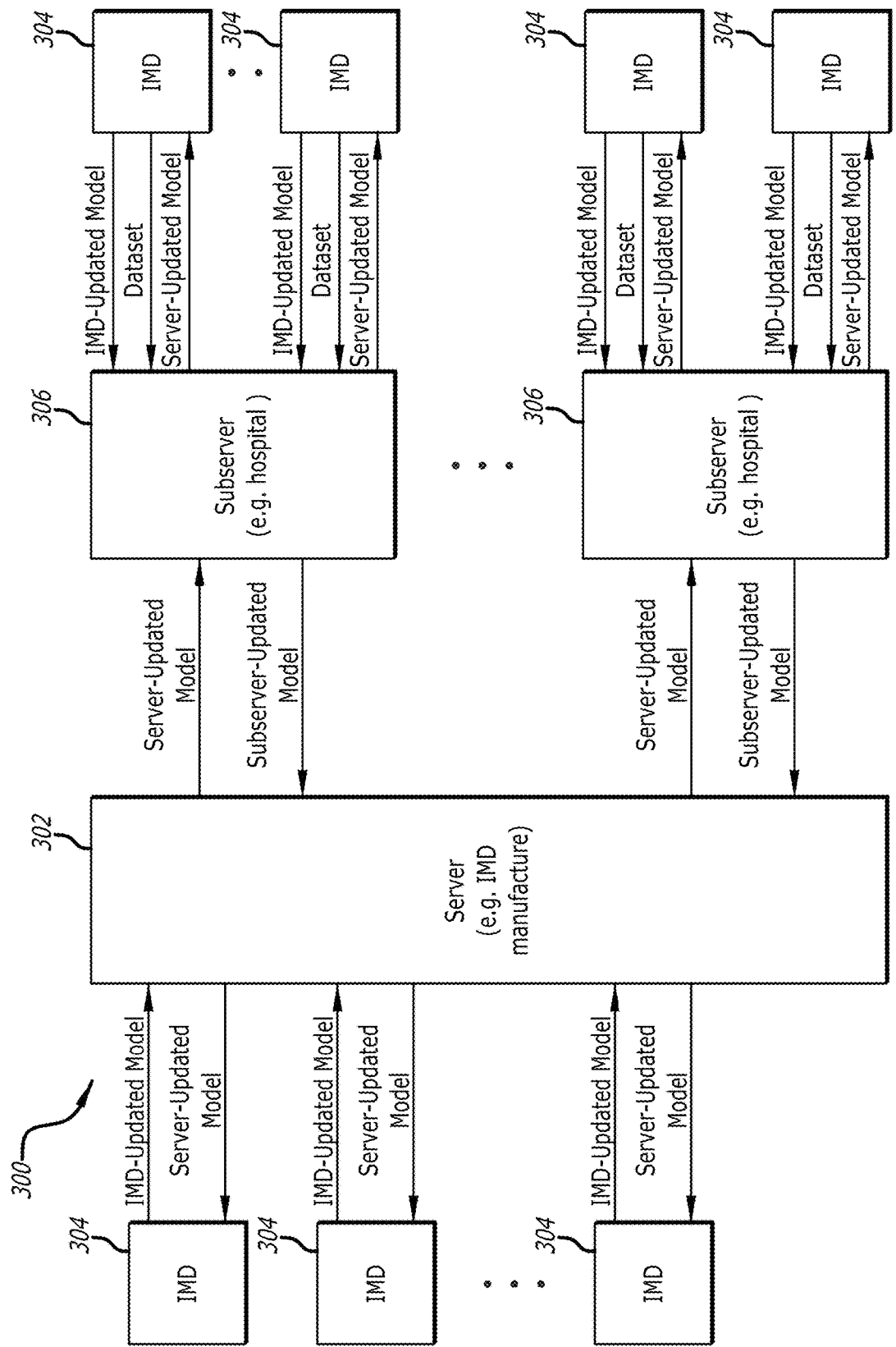
FIG. 3 is a block diagram of a training system for generating updated models of algorithms for implanted medical devices (IMD) based on federated learning under either of a first scenario that involves the application of machine learning to raw data at the device level, and a second scenario that involves the application of machine learning to raw data at an intermediate or subserver level between the device and a main server.

FIG. 3 is a block diagram illustration of a training system 300 for updating a machine learning model resident in a number of implanted medical devices 304. The training system includes a server 302 and a plurality of implanted medical devices 304. The training system 300 may also include one or more subservers 306. While FIG. 3 illustrates a limited number of implanted medical device 304 and subservers 306, the training system 300 may include more of these components. For example, a training system may include tens of thousands of implanted medical devices 304.

The implanted medical devices 304 are configured to capture and preserve physiological information of the patient in whom they are implanted and to use this information to train and update machine learning models resident in the device. For example EEG signals may be captured and preserved by an implanted medical device 304 in the form of one or more EEG records, such as represented in FIGS. 2A and 2B. Other types of physiological information as previously described may be captured and preserved by an implanted medical device 304 as physiological records. Collectively, the EEG records and other physiological records preserved by an implanted medical device 304 correspond to a dataset for the patient in whom the device is implanted. Typically, some sort of linkage or mapping among the various types of physiological information is provided in the dataset. For example, a time based mapping may be provided, wherein each record in a dataset is time stamped (such as shown in FIG. 2B) so that all physiological information at a given point in time may be gathered and used by the training system 300.

In the training system 300 disclosed herein, an implanted medical device 304 may correspond to an implanted neurostimulation system that includes implantable components, namely, an active medical device or neurostimulator, and one or more electrode-bearing leads. The electrodes are configured to rest in or on neural tissue in the patient's brain when the leads are implanted. The neurostimulator may be configured to be implanted in or on the patient's cranium or elsewhere in the patient, e.g., pectorally. Once the neurostimulator is implanted, each lead is connected to the neurostimulator. The combination of the implanted neurostimulator and the implanted lead(s) is configurable to sense physiological signals in the form of EEG signals and process and store records of the EEG signals to thereby create a dataset of EEG records for the patient in whom the neurostimulation system 304 is implanted. From these signals, the implanted neurostimulation system 304 may derive other physiological information. For example, EEG signals may include information indicative of the sleep state of the patient and the sleep patterns of the patient.

An implanted neurostimulation system 304 may also be configured to sense and record other types of physiological signals besides EEG signals. To this end, the implanted neurostimulation system 304 may include a lead as disclosed in U.S. Pat. No. 10,390,721, entitled Multimodal Brain Sensing Lead, which is herein incorporated by reference. Such a multimodal brain sensing lead may include: (1) macroelectrodes; (2) microelectrodes; (3) light emitters; and (4) photodetectors. Different sensing modalities of the implanted neurostimulation system 304 use the different transducers as follows: (1) neuronal field potential measurements are made using macroelectrodes; (2) neuronal single unit activity measurements are made using microelectrodes; (3) neuronal multi-unit activity measurements are also made using microelectrodes; (4) rheoencephalography measurements are made using macroelectrodes; (5) neurochemical and pharmaceutical voltammetric measurements are made using both macroelectrodes and microelectrodes; (6) optical blood flow and volume measurements are made using light emitters and photodetectors; and (7) optical blood oxygenation measurements are also made using light emitters and photodetectors.

Configured as such, the implanted neurostimulation system 304 may sense and record signals indicative of blood oxygen level and blood volume in neural tissue, and signals indicative of chemical concentrations and neurotransmitter concentrations in neural tissue. From these signals, the implanted neurostimulation system 304 may derive other physiological information. For example, blood flow, blood oxygenation, blood pressure, heart rate, and breathing rate may be estimated from blood oxygen and blood volume measurements, while pH levels and blood glucose levels may be derived from chemical concentrations and neurotransmitter concentrations.

The implanted neurostimulation system 304 may also include one or more electrodes configured to sense electrical cardiac activity indicative of heart rate, a pressure sensor configured to provide signals indicative of blood pressure, an accelerometer and gyroscope configured to provide motion signals indicative of motion and the position of the patient. From these accelerometer and gyroscope signals, the implanted neurostimulation system 304 may derive other physiological information corresponding to clinical seizures, patient posture, and sleep state.

Other types of physiological information may be obtained and stored by the implanted neurostimulation system 304 from sources independent of the neurostimulation system. For example, an external wearable device, e.g., patch, may include a sensor configured to sense and track cortisol levels, i.e., stress hormones in sweat, while an external wearable device, e.g., watch, may include a sensor configured to measure blood pressure. The physiological information from these external devices may be communicated to the implanted neurostimulation system 304 for inclusion in the patient's dataset.

Regarding EEG records, the neurostimulator may be configured to record an EEG signal as a time series of digital data samples, and to store them in a memory. The time series of digital data samples of an EEG record can be used to generate or transform the EEG record into other formats. A non-exhaustive list of other possible EEG record formats includes a time-series waveform image of an EEG record (such as shown in FIGS. 2A and 2B) or a Fourier or wavelet transformed version of the time-series EEG record. Each such EEG record also can be transformed (by well-known techniques) into other formats such as a time-frequency spectrogram (such as shown in FIG. 2A) and used in that form. The database can be configured to create an EEG record in the desired form, e.g., time-series waveform or spectrogram, whenever the particular form of the EEG record is called for by an algorithm (e.g., to display it to a clinician and/or use it in a deep learning model). Systems and methods disclosed herein may operate on different formats of the EEG recording. For example, a deep learning model may process images of EEG signals, such as time-series images or a spectrogram images.

Records of physiological information may be generated by the implanted neurostimulation system 304 based on an occurrence of a triggering event. To this end, a neurostimulation system 304 can be configured to store an EEG record of a sensed EEG when an event the system is programmed to detect is detected. For example, the implanted neurostimulation system 304 may be configured to detect events from a sensed EEG corresponding to: 1) ictal activity, e.g., an electrographic seizure, or 2) pre-ictal activity, e.g. the onset of an electrographic seizure, and to store the corresponding EEG signal as an EEG record. Such EEG record may include, for example, a portion of the corresponding EEG signal spanning the time period 60 seconds before the event was detected and 30 seconds thereafter.

The neurostimulation system 304 may also be programmed to store an EEG record of a sensed EEG at certain times of day (e.g., at noon and at midnight). These are sometimes referred to as "scheduled EEGs." Such EEG record may include a specified duration, e.g., 90 seconds, of the sensed EEG. In addition, the neurostimulation system 304 may be configured to store an EEG record upon an external event, such as when the patient swipes a magnet over the location on the patient's body at which the neurostimulator is implanted and the magnetic field is detected by a magnetic sensor in the neurostimulator. The patient might be instructed to do this whenever he or she thinks a seizure is imminent. These are sometimes referred to as "patient-initiated EEGs." Such EEG records may include a portion of the EEG signal spanning the time period 60 seconds before the magnetic swipe was detected and 30 seconds thereafter.

The neurostimulation system 304 may also be programmed to designate EEG records based on the event that triggered its recording and to include that designation in the EEG record, together with the time of the event. For example, with reference to FIGS. 2A and 2B, EEG records resulting from the detection of abnormal electrical activity corresponding to ictal activity, e.g., an electrographic seizure, may be labeled as "ictal" or "seizure" records. EEG records resulting from the detection of abnormal electrical activity corresponding to pre-ictal activity, e.g., an onset of an electrographic seizure, may be marked as "pre-ictal" records. EEG records that do not reflect abnormal electrical activity may be designated as "baseline" records, "not seizure" records, or "interictal" records. EEG records resulting from a schedule may be designated as a scheduled EEG, while EEG records resulting from a magnetic swipe may be designated as a patient-initiated EEG.

The neurostimulation system 304 may also be programmed to derive additional characteristics from the EEG signals included in the EEG records. For example, the neurostimulation system 304 may be configured to process sensed EEG signals to derive measures related to spectral power in the signal, the rate of occurrences of electrographic spikes in the signals, the occurrences of long episodes in the signals, the rate of occurrences and/or the durations of long episodes in the signals.

Thus, for a given patient, a dataset may contain EEG records corresponding to (1) activity in the patient's brain during and around when an event occurs, (2) scheduled EEG records acquired at a particular time, and (3) EEG records stored by the neurostimulator when a patient triggers storage with a magnet. Some of these EEG records, especially the ones recorded at the time of an event or when triggered by a magnet swipe, may reflect the patient's electrographic seizures. The dataset may include information concerning the event that triggered the storing of the EEG record. This information may indicate whether the EEG record resulted from detection of an electrographic event (e.g., a pattern of abnormal electrical activity or epileptiform activity representative of ictal activity or pre-ictal activity), a magnet swipe, or a schedule, together with the time of such event. The dataset may also include additional information describing characteristics of the EEG signals included in the EEG records, such power metrics, occurrences of long episodes, etc., as the previously described.

Typically, some sort of linkage or mapping among the various types of physiological information is provided in a dataset. To this end, each record may have one or more associated tags or parameters. For example, physiological records may have a time stamp that allows a set of physiological records at a given point in time to be located for processing. Physiological records may have a tag that indicates the basis, e.g., seizure detection, seizure onset detection, magnet swipe, scheduled time of day, for preserving the record. These tags allow a set of physiological records to be selected for processing based on a single criterion or a combination of criteria. Other tags may include time and date of capture, area of the brain at which the electrical activity of EEG record was captured, trigger for record creation (e.g., seizure detection, seizure onset detection, scheduled, patient initiated), or a derived characteristic of the record (e.g., power spectral density of EEG signal prior to stimulation, long episode EEG signal, etc.).

Once created by an implanted neurostimulation system 304, a patient's dataset may be relayed elsewhere, such as to an external component like a subserver 306 either directly or through an intermediate external component. For example, an external patient monitor can be used to establish a communications link with the implanted neurostimulator (e.g., a short-range telemetry link), which allows a dataset stored in the neurostimulator to be transmitted to the patient monitor. Once in the patient monitor, the dataset can be transmitted to the subserver 306 via a communications network.

Alternatively, the clinician may be provided with an external component, such as a programmer that, like the patient monitor, is configured to establish a communications link with the implanted neurostimulator. The programmer may be used to acquire a dataset stored in the neurostimulator. Once a dataset is stored in a programmer, it can be transmitted via the network to a subserver 306.

The dataset stored locally in the neurostimulator, patient monitor, or programmer, or transmitted to a subserver 306, may be referred to herein as a decentralized dataset since it is not shared with or transmitted to a central server 302 of the training system 300. The data within the dataset stored locally in the neurostimulator, patient monitor, or programmer, or transmitted to a subserver 306, is raw data from the patient in whom the neurostimulator is implanted.

Some or all of the implanted neurostimulation system 304 included in the training system 300 may be configured to deliver electrical stimulation therapy in response to "events" that the neurostimulator is configured to detect. An event may be defined for the neurostimulator by setting the values of programmable detection parameters such that when a pattern of electrical activity corresponding to a pattern defined by the detection parameters occurs in a monitored EEG signal, the occurrence of that pattern will be detected as an event. In some embodiment, the patterns may be indicative of ictal activity, e.g., a seizure, or pre-ictal activity, e.g., a seizure onset. Some implantable neurostimulation systems 304 included in the training system 300 may not have the feature of responsive neurostimulation at all or may not have it enabled.

Training System Operation Scenarios

With reference to FIG. 3, the training system 300 may generate updated models of algorithms for implanted medical devices 304 based on federated learning under either of a first scenario that involves the application of machine learning to raw data at the device level, or a second scenario that involves the application of machine learning to raw data at an intermediate or subserver 306 level between the implanted medical devices 304 and a main server 302. In either scenario, raw data is not sent to or otherwise shared with the main server 302.

First Scenario—Federated Learning at the Implanted Medical Device Level

Figure 4:
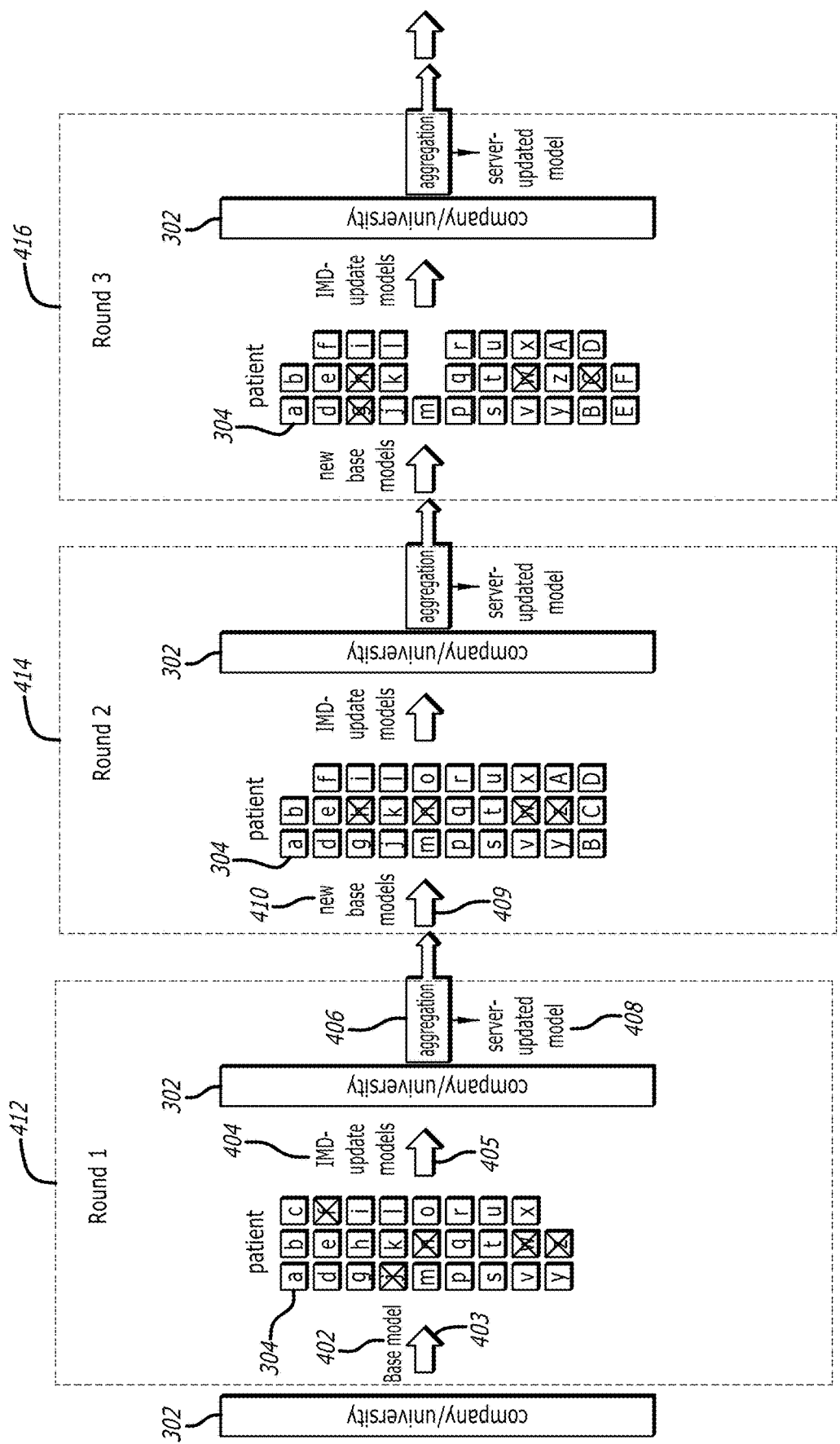
FIG. 4 is a detailed block diagram of the first scenario of FIG. 3 that involves the application of machine learning to raw data at the device level.

With reference to FIG. 4, in the first scenario, a base model 402 is present in a plurality of individual implanted medical devices 304, each implanted in a respective patient a-z. The base model 402 is maintained at a main or central server 302 by an entity, which may be the medical device manufacturing company. The base model 402 may be loaded 403 into an implantable medical device 304 before the device is implanted in individual patients a-z or it may be programmed or downloaded on the device after implant, such as during a hospital visit. The base model 402 may be built by the medical device manufacturing company by analyzing previously collected data in a similar patient population. The base model 402 may also be built by analyzing simulated patient data, or by performing a literature review.

Figure 5:
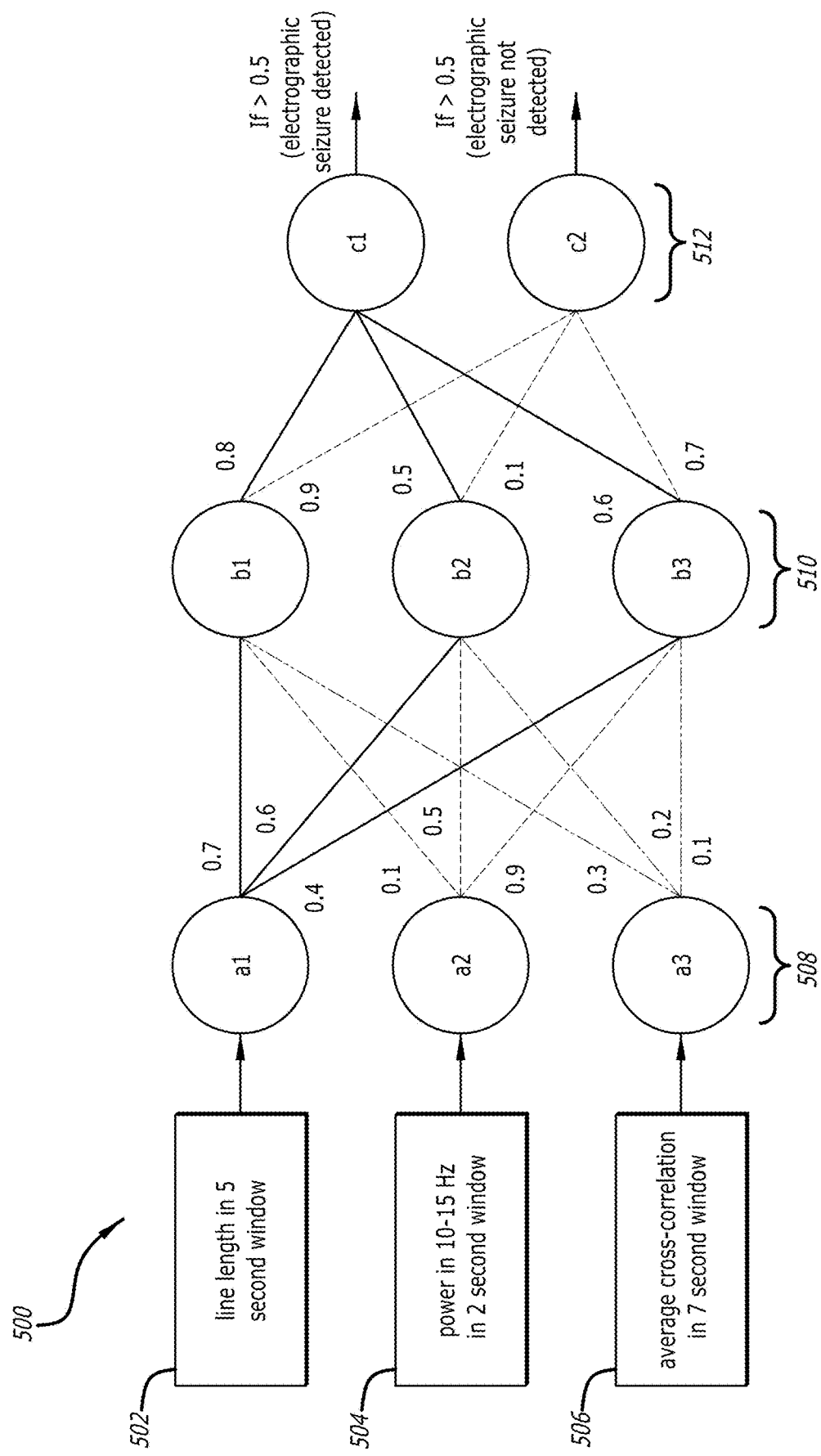
FIG. 5 is an illustration of a model in the form of a three-layer deep neural network for seizure detection that is trained on features extracted from an EEG signal, including a line length feature, a power feature, and a cross-correlation feature.

With reference to FIG. 5, in one example, a base model is a three-layer deep neural network model 500 for seizure detection that is trained on features extracted from an EEG signal, including a line length feature, a power feature, and a cross-correlation feature. The first layer 508 of the three-layer deep neural network 500 includes three neurons a1, a2, a3 that respectively receive one of the extracted features as an input 502, 504, 506. These three first-layer neurons a1, a2, a3 are connected to three neurons b1, b2, b3 in a second layer 510, which in turn are connected to two neurons c1, c2 in the third, output/final layer 512 of the neural network model 500.

The three-layer deep neural network model 500 may be built based on either a training dataset available to the server 302 or simulated data. In the example three-layer deep neural network model 500, a first input 502 corresponding to a line length in 5 second windows of an EEG signal, a second input 504 corresponding to power in 10-15 Hz in 2 second windows of an EEG signal, and a third input 506 corresponding to an average cross-correlation in 7 second windows of an EEG signal are determined by the company maintaining the server 302 to be important features for training supervised machine learning models for seizure detection. Other features that may be extracted and used as inputs include but are not limited to the area under the curve of a portion of an EEG signal, the line length (i.e., the sum of the absolute value of sample-to-sample voltage differences) of a portion of an EEG signal, the total number of half waves in a portion of an EEG signal, the number of half waves in a portion of an EEG signal that meet specific criteria, the number of electrographic spikes in a portion of an EEG signal, the total spectral power in a portion of an EEG signal, the spectral power within specific frequency bands of a portion of an EEG signal, the RMS (root mean square) of voltages in a portion of an EEG signal, a measure of coherence between different portions of an EEG signal, a measure of synchrony among different portions of an EEG signal, and a measure of entropy of a portion of an EEG signal. The specific choice of inputs to the neural network model 500 are selected to optimize performance of the neural network.

These inputs 502, 504, 506 may be extracted from EEG records in a training dataset using known techniques. For example, a deep learning model may be applied to each EEG record to extract features from that record. While the exact nature or characteristics of the features extracted from the physiological records by the deep learning model are not entirely understood, the features are believed to include hierarchically filtered versions of the data forming the record. The deep learning model may be, for example, a pre-trained convolutional neural network (CNN), autoencoders, recurrent neural network (RNN), or a deep neural network configured to derive features from the physiological records. These deep learning models are described in Deep Learning, by Yann LeCun, Yoshua Bengio and Geoffrey Hinton. Nature, published May 27, 2015, Volume 521, pp 436-444.

Feature extraction may also be done through pre-trained deep learning models, such as AlexNet or Inception-v3; or by training the deep learning models from scratch. AlexNet is described in ImageNet Classification with Deep Convolutional Neural Networks, by A. Krizhevsky, I. Sutskever, and G. Hinton, included in Advances in Neural Information Processing Systems 25 (NIPS 2012), available at http://papers.nips.cc/paper/4824-imagenet-classification-with-deep-convolutional-neural-networks.

Other types of algorithms may be used to extract features. For example, handcrafted algorithms, such as spectral power algorithms, Fast Fourier Transform algorithms or wavelet features algorithms, may be used. Depending on the model architecture that is selected, dimensionality reduction may be performed to convert the input features to a format that is suitable for the model.

Alternatively, the raw EEG signals or a transform of the raw EEG signal computed using Fast Fourier Transform, for example, may be fed directly as input to the deep neural network. In such cases, the neural network used for training may be much larger with several layers and several neurons in each layer. If convolutional neural networks architectures are trained, tens or hundreds of convolutional filters in each layer may be trained.

The three-layer deep neural network model 500 is trained on the extracted features or raw EEG signals. Once training of the neural network model 500 is complete, trained neural network weights and biases are obtained, where biases are associated with the neurons a1-c2 and weights are associated with the interconnections between pairs of neurons. For simplicity, only the neural networks weights are shown in FIG. 5. Biases are not shown. For example after the training process, a weight of 0.7 is obtained for the connection between neuron a1 in the first layer and neuron b1 in the second layer.

While the three-layer deep neural network model 500 thus disclosed is trained on features extracted from EEG signals, other types of features may be used. Expanding the neural network model to include additional layers enables other types of physiological information to be input as training data. For example, other physiological information, e.g., blood flow, blood oxygenation, blood pressure, heart rate, breathing rate, pH levels, blood glucose levels, patient posture, sleep state, hormone level, mapped to EEG signals in a dataset may be used as inputs in a multi-layer neural network model. Non-physiological information included in a dataset, such as patient demographics (e.g., age, gender), drug regimen (e.g., type of drug, dose, and time of day of dose), and clinical outcomes, such as the rate of electrographic seizure detection and electrographic seizure onset, the rate of clinical seizures, may also be used as inputs in a multi-layer neural network model. Addition of other types of features may increase the accuracy of the resulting seizure detection and prediction models, since each additional feature may contain information about the patient's state that is not captured by the EEG signals alone.

While a deep neural network model is provided as an example architecture for building a base model 402, other types of architectures may be used, such as supervised machine learning classification and regression algorithms. Some examples are convolutional neural networks, recurrent neural networks, logistic regression, linear regression, support vector machines, decision trees and random forests. The architecture(s) selected for training may be hand-crafted i.e., entirely designed manually or may be designed using architecture search algorithms such as the neural architecture search algorithms (AutoML on Google Cloud Platform, for example).

Returning to FIG. 4, and continuing with the model update process under the first scenario, during a first round 412 of the process, the base model 402 resident in each of the participating implanted medical devices 304 is trained or built locally by the implanted medical device into an IMD-updated model 404. The IMD-updated models 404 are used in turn, by the server 302 to create a server-updated model 408 for upload to the implanted medical devices during a second round 414 of the process.

Continuing with the first round 412, each respective IMD-updated model 404 is built locally by a corresponding implanted medical device 304 using the physiological information included in the dataset collected and stored in that implanted medical device 304. Once an IMD-updated model 404 is built by an implanted medical device 304 the physiological information included in the dataset may be deleted to free up the space in the device for additional data storage. Some patients may be unwilling to have their physiological information used by the training system 300 and thus may opt out of having their implanted medical device 304 participate in the model update process. In some cases, an implanted medical device 304 may not participate in the model update process because it is not capable of performing the computations required for the model update. For example, in the first round 412 of FIG. 4, the implanted medical devices 304 associated with patients f, j, n, w, z are not participating in the model update process.

The implanted medical devices 304 participating in the model update process may be configured to automatically initiate updates of the base model 402. Such updates may be initiated synchronously across all implanted medical devices 304 participating in the model update process, or asynchronously. Synchronous updates may be initiated on participating implanted medical devices 304 on a fixed calendar date, e.g., the $1^{st}$ of every alternate month. Asynchronous updates on participating implanted medical devices 304 may be initiated at a different time for different devices, e.g., every two months, beginning from the date of implant of the device in the patient, or after a specified amount of new data has been added to the dataset of an implanted medical device. For example, an update may be initiated after 100 hours of new data has been added to a dataset. For some implanted medical devices 304 this amount of new data may be captured within 15 days, while in other devices it may take 1 year.

In the example above, where the base model 402 is a three-layer deep neural network 500 architecture as shown in FIG. 5, each participating implanted medical device 304 updates its base model by extracting features from the EEG records included in the dataset stored in the implanted medical device and training the neural network on the extracted features using additional information associated with the EEG records. This additional information may include labels, referred to herein sometimes as "training labels," that are indicative of the basis for the EEG record.

For example, a training label may indicate that the EEG record resulted due to a magnet swipe, which in turn, may be considered to indicate that the EEG signals included in the EEG record contains electrographic seizures. Hence EEG records associated with magnet swipes may be used as positive training examples and those without magnet swipes may be used as negative training examples for training an electrographic seizure detection algorithm. Other labels, such as those corresponding to a pattern of abnormal electrical activity or epileptiform activity representative of ictal activity, may be similarly used to identify EEG records having EEG signals that include electrographic seizures. The training tunes or adjusts the weights and biases of the three-layer deep neural network 500 to create an IMD-updated model 404 using training error backpropagation and optimization algorithms such as Stochastic Gradient Descent, Adam, Nadam for example.

Returning to FIG. 4, after an implanted medical device 304 creates an IMD-updated model 404, the IMD-updated model from that implanted medical device is transferred 405 to the server 302. This transfer 405 may occur automatically upon completion of a model update by the implanted medical device 304 or at a scheduled time. This transfer 405 may be directly from the implanted medical device 304 to the server 302, or may be through a surrogate of the device, such as a patient monitor or physician programmer.

The server 302 performs model aggregation 406 on the IMD-updated model 404 updates. To this end, the server 302 operates based on whether the IMD-updated models 404 are received from the participating implanted medical devices 304 synchronously or asynchronously. In the case where the server 302 receives the IMD-updated models 404 synchronously, e.g., IMD-updated models 404 received from all participating implanted medical devices 304 on the same calendar date, the server 302 may wait for one or two days to receive and store all IMD-updated models 404 in a data storage server controlled by the company. The IMD-updated models 404 may be sent to the server 302 through automatic uploads to the company's cloud-based database for example. If a particular implanted medical device 304 that is participating in the update process has not uploaded its IMD-updated model 404 to the server 302 within a reasonable time-window pre-specified by the company (for example within 2 calendar days), then the IMD-updated model 404 from that particular device may simply be omitted from the model aggregation.

In the case where the server 302 receives the IMD-updated models 404 asynchronously, e.g., automatically from each implanted medical device 304 after the device has built an IMD-updated model 404, the server waits until it receives a sufficient number of IMD-updated models before proceeding to perform model aggregation. For example, the server 302 may wait to receive IMD-updated models 404 from at least 1000 participating implanted medical devices 304 (or 100 subservers 306) before proceeding to perform model aggregation. If some implanted medical devices 304 send more than one IMD-updated model 404 during this time, the company may choose to use the latest IMD-updated model from the implanted medical devices 304 in its model aggregation step. In either case, once the server 302 is ready to aggregate all the IMD-updated models 404 received from the individual implanted medical devices 304, the server performs model aggregation 406 to create a server-updated model 408.

Continuing with the example three-layer deep neural network 500 architecture shown in FIG. 5, model aggregation 406 of IMD-updated models 404 based on this architecture may involve calculating an average, e.g., a naive average, of parameters of the IMD-updated models 404 and assigning the averages to corresponding parameters of the server-updated model 408. For example, a parameter of the IMD-updated model 404 may be a bias associated with a particular node, in which case the calculated average is assigned to that particular node in the server-updated model 408. In another example, a parameter of the IMD-updated model may be a weight associated with an interconnection between a pair of nodes, in which case the calculated average is assigned to that particular interconnection in the server-updated model 408.

A weighted averaging of the foregoing parameters, e.g., node biases and interconnection weights, may be performed wherein varying weights factors are given to the parameters of the IMD-updated models 404 based on the amount of data used to create the IMD-updated model. For example, higher weights may be given to the parameters of an IMD-updated model 404 created with a larger amount of training data compared to other IMD-updated models 404. See McMahan et al., "Communication-efficient learning of deep networks from decentralized data". Artificial Intelligence and Statistics, pp. 1273-1282, 2017.

Model aggregation 406 may involve other processes that precede averaging or weighted averaging. For example, probabilistic federated neural matching may be performed. In this process, neurons or nodes from individual IMD-updated models 404 are matched before the averaging. Nodes may be matched based on similar feature extraction signatures in a layer-wise approach. (See Yurochkin et al., "Bayesian nonparametric federated learning of neural networks." International Conference on Machine Learning, pp. 7252-7261, 2019b).

Model aggregation 406 may also involve federated matched averaging, which accounts for permutation invariance of neurons and permits global model size adaptation (See Wang et al., "Federated learning with Matched Averaging" International Conference on Learning Representations, 2020). Additionally, secure aggregation, a method to aggregate individual IMD models without exposing the individual IMD models' updates to the server, may be used. See Bonawitz et al., "Practical secure aggregation for privacy-preserving machine learning." Proceedings of the 2017 ACM SIGSAC Conference on Computer and Communications Security, pp. 1175-1191. 2017. In any case, the aggregation 406 of the IMD-updated models 404 results in the server-updated model 408.

The server 302 may be configured to test the server-updated model 408 on test data, which may be simulated, or real patient data that the company possesses. If performance of the server-updated model 408 is worse than the performance of the base model 402 the server 302 may reject the server-update model in the first round 412, e.g., refrain from uploading it to the implanted medical devices 304, and move on to the second round 414. If on the other hand, the server 302 accepts the server-updated model 408 based on for example the model's performance on test data, the server 302 sends out 409 the server-updated model 408 as the new base model 410.

Additional rounds 414, 416 of model updates may be performed, where each round repeats the model updating process of the first round 412. This process continues and the training system 300 may perform several model updates in this manner without actually having possession of any of the training patient's raw data. Note that in subsequent model update rounds 414, 416 new implanted medical device 304 of new patients may be added or existing implanted medical device 304 of existing patients may drop out for various reasons. For example, between the first round 412 and the second round 414 the implanted medical devices 304 associated with patients f and j changed from non-participating to participating, while the implanted medical device 304 associated with patient h changed from participating to non-participating device. And the implanted medical devices 304 associated with new patients A-D joined as new participating devices.

Second Scenario—Federated Learning at an Intermediate Level

Figure 6A:
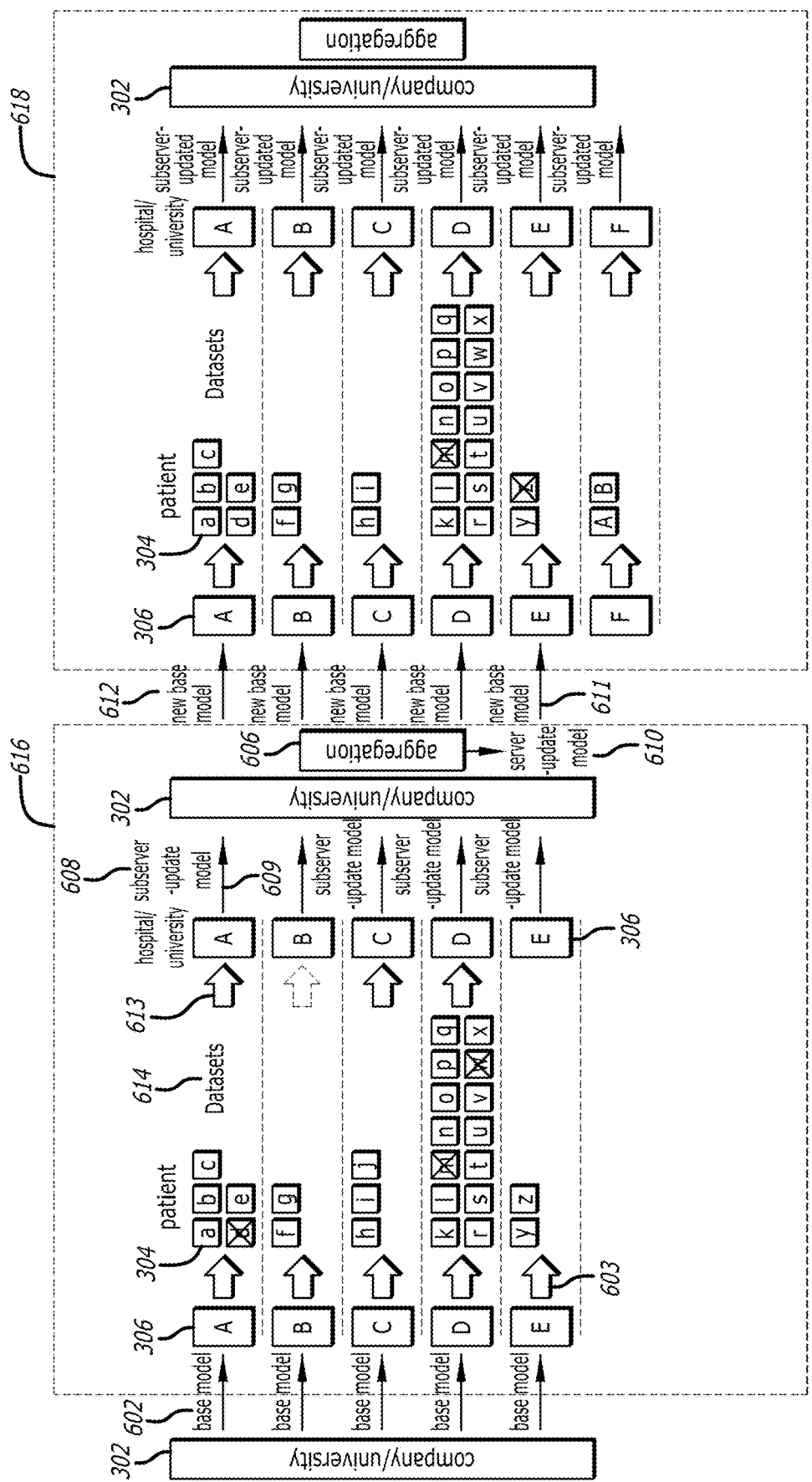
FIGS. 6A and 6B are detailed block diagrams of the second scenario of FIG. 3 that involves the application of machine learning to raw data at an intermediate or subserver level between the device and a main server.
Figure 6B:
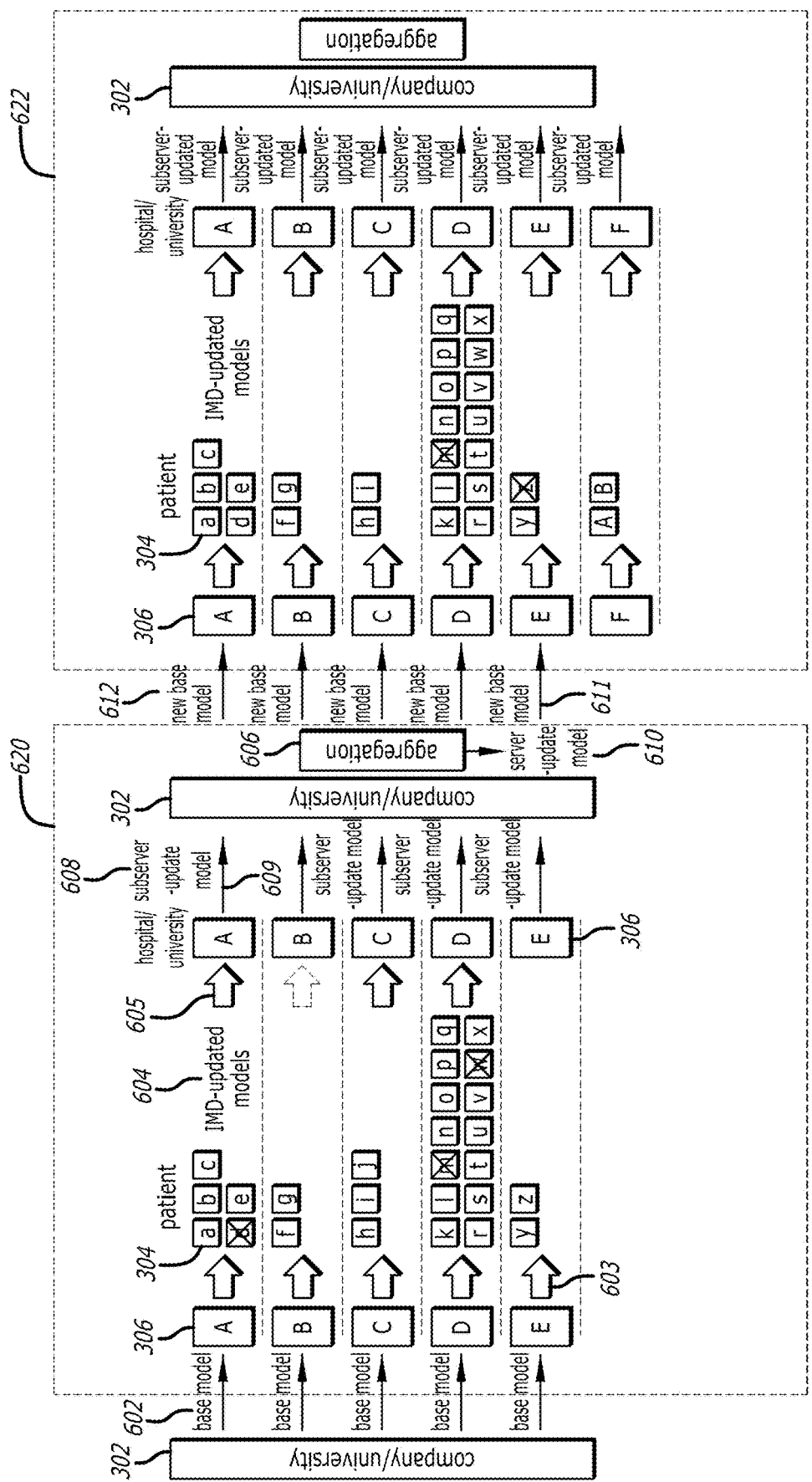

With references to FIGS. 6A and 6B, in a second scenario, a base model 602 is present in a plurality of individual implanted medical devices 304, each implanted in a respective patient a-z. The base model 602 is maintained at a main or central server 302 by an entity, which may be the medical device manufacturing company. The base model 602 is provided to an apparatus, referred to as a subserver 306, that is intermediate the central server 302 and the implanted medical devices 304. The subserver 306 may be located, for example, at a hospital A-E. The base model 602 may be loaded 603 by the respective subserver 306 into an implantable medical device 304 before the device is implanted in individual patients a-z or it may be programmed or downloaded on the device after implant. The base model 602 may be built as described above with reference to FIG. 5 under the first scenario of federated learning.

A model update process under the second scenario may be implemented with a single-stage federated learning process or a two-stage federated learning process. In a single-stage federated learning process the model updates are handled by subservers 306 with federated learning taking place at the server 302. In a two-stage federated learning process the model updates are handled by the implanted medical devices 304 with a first-stage federated learning taking place at the subserver 306, followed by a second-stage federated learning taking place at the server 302.

Single-Stage Federated Learning

With continued reference to FIG. 6A, in a single-stage federated learning process, during a first round 616 the base model 602 resident in each of the participating subservers 306 is updated locally by the subserver into a subserver-updated model 608. To this end, each participating implanted medical device 304 associated with a participating subserver 306 sends 613 its dataset 614 to its associated subserver, where the datasets are pooled together into a single dataset. Each respective subserver-updated model 608 is built locally by a corresponding participating subserver 306 using the physiological information included in the datasets 614 it receives. The subserver-updated model 608 may be built in the same manner the IMD-updated models are built, as described above in the first scenario. Again, some patients may be unwilling to have their physiological information used by the training system 300 and thus may opt out of having their implanted medical device 304 participate in the model update process. In some cases, an implanted medical device 304 may not participate in the model update process because it is not capable communicating with the subserver for the model update. For example, in the first round 616 of FIG. 6A, the implanted medical devices 304 associated with patients d, m, and w are not participating in the model update process.

Furthermore, one or more subservers 306 may not participate in a model update process. For example, some hospitals A-E may choose to not participate in the model update process or some hospitals may not have the necessary infrastructure/resources to perform the model updates. In the first round of FIG. 6A, the subserver 306 associated with hospital B is not participating in the update process. Such subserver 306 may not receive datasets 614 from its associated implanted medical devices 304. Alternatively, the subserver 306 may receive datasets 614 from its associated implanted medical devices 304 but do nothing further with the datasets.

The subservers 306 participating in the model update process may be configured to automatically initiate updates of the base model 602 in the manners as the implanted medical devices 304 initiate updates of the base model, as described above in the first scenario. Such updates may be initiated synchronously across all subservers 306 participating in the model update process, or asynchronously, as described above in the first scenario.

After a subserver 306 creates a subserver-updated model 608, the subserver-updated model from that subserver is transferred 609 to the server 302. This transfer 609 may occur automatically upon completion of a model update by the subserver 306 or at a scheduled time.

The server 302 performs model aggregation 606 on the subserver-updated models 608. To this end, the server 302 operates based on whether the subserver-updated models 608 are received from the participating subserver 306 synchronously or asynchronously. In the case where the server 302 receives the subserver-updated models 608 synchronously, the server 302 may wait for one or two days to receive and store all subserver-updated models 608 in a data storage server controlled by the company. The subserver-updated models 608 may be sent to the server 302 through automatic uploads to the company's cloud-based database for example. If a particular subserver 306 that is participating in the update process has not uploaded its subserver-updated models 608 to the server 302 within a reasonable time-window pre-specified by the company (for example within 2 calendar days), then the subserver-updated models 608 from that particular subserver may simply be rejected.

In the case where the server 302 receives the subserver-updated models 608 asynchronously the server waits until it receives a sufficient number of subserver-updated models before proceeding to perform model aggregation. For example, the server 302 may wait to receive subserver-updated models 608 from at least 100 participating subservers 306 before proceeding to perform model aggregation. If a subserver 306 sends more than one subserver-updated model 608 during this time, the company may choose to use the latest subserver-updated model from that subserver in its model aggregation step. In either case, once the server 302 is ready to aggregate all the subserver-updated models 608 received from the subservers 306, the server performs model aggregation 606 to create a server-updated model 610.

The model aggregation performed by the server 302 may be the same as the model aggregation performed by the server under the first scenario (i.e., federated learning at the implanted medical device level). For example, in the case of a three-layer deep neural network 500 architecture as shown in FIG. 5, model aggregation 606 of subserver-updated models 608 may involve taking the average, e.g., naive average, of the trained model weights from the plurality of IMD-updated models and assigning the averages to the model. Alternatively a weighted averaging may be performed where more weight is given to subserver-updated models 608 created with more training data. For example, more weight may be given to a subserver-updated model 608 that was built by a subserver 306 associated with a hospital that has more participating implanted medical devices 304. Alternatively, other aggregation methods such as Probabilistic Federated Neural Matching or Federated Matched Averaging described previously may be used for model aggregation.

The server 302 may be configured to test the server-updated model 610 on test data, which may be simulated or real patient data, that the company possess. If performance of the server-updated model 610 is worse than the performance of the base model 602 the server 302 may reject the server-update model in the first round 616, e.g., refrain from uploading it to the implanted medical devices 304, and move on to the second round 618. If on the other hand, the server 302 accepts the server-updated model 610 based on for example the model's performance on test data, the server 302 sends out 611 the server-updated model 610 as the new base model 612. The new base model 612 may be sent to the subservers 306 participating in the model update process. Each subserver 306, in turn, sends the new base model 612 to the implanted medical devices 304 associated with that server.

Additional rounds 618 of model updates may be performed, where each round repeats the model updating process of the first round 616. This process continues and the training system 300 may perform several model updates in this manner without actually having possession of any of the training patients' raw data. Note that in subsequent model update rounds new implanted medical devices 304 of new patients may be added and new subservers 306 may be added or existing implanted medical device 304 of existing patients may drop out for various reasons or existing subservers may drop out.

Two-Stage Federated Learning

With reference to FIG. 6B, in a two-stage federated learning process, during a first round 620 the base model 602 resident in each of the participating implanted medical devices 304 is updated locally by the implanted medical device into an IMD-updated model 604. Each of a respective set of IMD-updated models 604 is used by a respective subserver 306 to create a corresponding subserver-updated model 608 based on the IMD-updated models. This is the first of the two stages of federated learning. The subserver-updated models 608 are then used by the server 302 to create a server-updated model 610 for upload to the implanted medical devices 304. This is the second of the two stages of federated learning.

Each respective IMD-updated model 604 is built locally by a corresponding participating implanted medical device 304 using the physiological information included in the dataset collected and stored in that implanted medical device 304, as described above in the first scenario. Again, some patients may be unwilling to have their physiological information used by the training system 300 and thus may opt out of having their implanted medical device 304 participate in the model update process. In some cases, an implanted medical device 304 may not participate in the model update process because it is not capable of performing the computations required for the model update. In the first round 620 of FIG. 6B, the implanted medical devices 304 associated with patients d, m, and w are not participating in the model update process.

Furthermore, one or more subservers 306 may not participate in a model update process. For example, some hospitals A-E may choose to not participate in the model update process or some hospitals may not have the necessary infrastructure/resources to perform the model updates. In the first round 620 of FIG. 6B, the subserver 306 associated with hospital B is not participating in the update process. Such subserver 306 may not receive IMD-updated models 604 from its associated implanted medical devices 304. Alternatively, the subserver 306 may receive IMD-updated models 604 from its associated implanted medical devices 304 but do nothing further with the updated models.

The implanted medical devices 304 participating in the model update process may be configured to automatically initiate updates of the base model 602, as described above in the first scenario. Such updates may be initiated synchronously across all implanted medical devices 304 participating in the model update process, or asynchronously, as described above in the first scenario.

After an implanted medical device 304 creates an IMD-updated model 604, the IMD-updated model from that implanted medical device is transferred 605 to the subserver 306. This transfer 605 may occur automatically upon completion of a model update by the implanted medical device 304 or at a scheduled time. This transfer 605 may be directly from the implanted medical device 304 to the subserver 306, or may be through a surrogate of the device, such as a patient monitor or physician programmer.

Each participating subserver 306 performs model aggregation on the set of IMD-updated models 604 that it receives. To this end, the subserver 306 operates based on whether the IMD-updated models 604 are received from the participating implanted medical devices 304 synchronously or asynchronously. In the case where the subserver 306 receives the IMD-updated models 604 synchronously, e.g., IMD-updated models 604 received from all participating implanted medical devices 304 on the same calendar date, the subserver 306 may wait for one or two days to receive and store all IMD-updated models 604 in a data storage server controlled by the entity, e.g., hospital, maintaining the subserver 306. The IMD-updated models 604 may be sent to the subserver 306 through automatic uploads to the entity's cloud-based database for example. If a particular implanted medical device 304 that is participating in the update process has not uploaded its IMD-updated model 604 to the subserver 306 within a reasonable time-window pre-specified by the entity (for example within 2 calendar days), then the IMD-updated model 604 from that particular device may simply be rejected.

In the case where a subserver 306 receives the IMD-updated models 604 asynchronously, e.g., automatically, from an implanted medical device 304 after the device has built an IMD-updated model, the subserver waits until it receives a sufficient number of IMD-updated models before proceeding to perform model aggregation. For example, the subserver 306 may wait to receive IMD-updated models 604 from at least 1000 participating implanted medical devices 304 before proceeding to perform model aggregation. If some implanted medical devices 304 send more than one IMD-updated model 604 during this time, the entity may choose to use the latest IMD-updated model from each implanted medical devices 304 in its model aggregation step. In either case, once a subserver 306 is ready to aggregate all the IMD-updated models 604 received from the individual implanted medical devices 304, the subserver performs model aggregation to create a subserver-updated model 608. The model aggregation performed by the subserver 306 may be the same as the model aggregation performed by the server 302 under the first scenario of FIG. 6A.

After subserver 306 creates a subserver-updated model 608, the subserver-updated model is transferred 609 to the server 302. This transfer 609 may occur automatically upon completion of the subserver-updated model 608 by the subserver 306 or at a scheduled time.

The server 302 performs model aggregation 606 on the subserver-updated models 608. To this end, the server 302 operates based on whether the subserver-updated models 608 are received from the participating subserver 306 synchronously or asynchronously. In the case where the server 302 receives the subserver-updated models 608 synchronously, the server 302 may wait for one or two days to receive and store all subserver-updated models 608 in a data storage server controlled by the company. The subserver-updated models 608 may be sent to the server 302 through automatic uploads to the company's cloud-based database for example. If a particular subserver 306 that is participating in the update process has not uploaded its subserver-updated models 608 to the server 302 within a reasonable time-window pre-specified by the company (for example within 2 calendar days), then the subserver-updated models 608 from that particular subserver may simply be rejected.

In the case where the server 302 receives the subserver-updated models 608 asynchronously the server waits until it receives a sufficient number of subserver-updated models before proceeding to perform model aggregation. For example, the server 302 may wait to receive subserver-updated models 608 from at least 100 participating subservers 306 before proceeding to perform model aggregation 606. If a subserver 306 sends more than one subserver-updated model 608 during this time, the company may choose to use the latest subserver-updated model from that subserver in its model aggregation step. In either case, once the server 302 is ready to aggregate all the subserver-updated models 608 received from the subservers 306, the server performs model aggregation 606 to create a server-updated model 610.

The model aggregation performed by the server 302 may be the same as the model aggregation performed by the server under the first scenario of FIG. 6A (i.e., federated learning at the implanted medical device level). For example, in the case of a three-layer deep neural network 500 architecture as shown in FIG. 5, model aggregation 606 of subserver-updated models 608 may involve taking the naive average of the trained model weights from the plurality of IMD-updated models and assigning them to the model. Alternatively a weighted averaging may be performed where more weight is given to subserver-updated model 608 created with more training data. For example, more weight may be given to a subserver-updated model 608 that was built by a subserver 306 associated with a hospital that has more participating implanted medical devices 304. Alternatively, other aggregation methods such as Probabilistic Federated Neural Matching or Federated Matched Averaging described previously may be used for model aggregation.

With reference to FIG. 7, example weights associated with the three-layer deep neural network 500 architecture as shown in FIG. 5 are provided for the base model 602, subserver-updated models 608 built by subservers 306 associated with hospitals A, B, C, and E, and the server-updated model 610. Each of the subservers 306 fine-tunes the base model 602 based on the data captured in its patients. Note that weights of the subserver-updated models 608 sent by the subservers 306 to the server 302 may be different from the weights of the base model 602. In this example implementation, the server 302 aggregates these subserver-updated models 608 by simply taking an average of each of the model weights to thereby create a server-updated model 610. Note that the weights of the server-updated model 610 are different from the weights of the base model 602.

Returning to FIG. 6B, the server 302 may be configured to test the server-updated model 610 on test data, which may be simulated or real patient data, that the company possess. If performance of the server-updated model 610 is worse than the performance of the base model 602 the server 302 may reject the server-update model in the first round 620, e.g., refrain from uploading it to the implanted medical devices 304, and move on to the second round 622. If on the other hand, the server 302 accepts the server-updated model 608 based on for example the model's performance on test data, the server 302 sends out 611 the server-updated model 610 as the new base model 612. The new base model 612 may be sent to the subservers 306 participating in the model update process. Each subserver 306, in turn, sends the new base model 612 to the implanted medical devices 304 associated with that server.

Additional rounds 622 of model updates may be performed, where each round repeats the model updating process of the first round 620. This process continues and the training system 300 may perform several model updates in this manner without actually having possession of any of the training patients' raw data. Note that in subsequent model update rounds new implanted medical devices 304 of new patients may be added and new subservers 306 may be added or existing implanted medical device 304 of existing patients may drop out for various reasons or existing subservers may drop out.

IMD-Updated Models

Data used by a particular implanted neurostimulation system 304 to train or update a base model to an IMD-updated model 404, 604 may vary in individual systems based on individual patient preferences or treating physician preferences. For example, for a model corresponding to a seizure detection or prediction algorithm, training data used to update such a model includes EEG records and labels that classify each EEG record as one of "seizure" or "non-seizure." As previously described, labels may be associated with or assigned to an EEG record in different ways. Accordingly, multiple implanted medical devices 304 associated with the same server 302 or the same subserver 306, e.g., hospital server, may use different methods of labeling seizure data and non-seizure data.

For example, a first patient having an implanted medical device 304 that is included in a training system 300 of a particular hospital may prefer maintaining detailed electronic records of "seizure" and "non-seizure" timings in a diary. In this case, the EEG records corresponding to EEG signals captured during "seizure" and "non-seizure" diary entries are assigned the "seizure" and 'non-seizure' labels respectively by the implanted neurostimulation system 304.

In another example, a second patient having an implanted medical device 304 that is included in the training system 300 of the particular hospital may prefer wearing a smart watch with an accelerometer. The implanted neurostimulation system 304 and smart watch are configured to communicate and operate together such that when the accelerometer readings exceed a threshold value, which may be patient-specific, the implanted neurostimulation system is notified, an EEG record corresponding to EEG signals captured while the threshold is exceeded is created and assigned a 'seizure' label by implanted neurostimulation system 304. All other EEG records are assigned a 'non-seizure' label. This may be the case in patients with generalized seizures where seizures are associated with convulsions.

In another example, a third patient having an implanted medical device 304 that is included in the training system 300 of the particular hospital, may trigger creation of an EEG record every time the patient experiences a clinical seizure. This may be done using a magnet swipe. In this case, the EEG records corresponding to EEG signals captured in response to a magnet swipe are assigned a 'seizure' label, while all other EEG records are assigned a 'non-seizure' label.

For a particular implanted medical device 304, it may take several months or even years to generate sufficient patient-specific training data from the patient to be able to update the base model of that system to an IMD-updated model 404, 604. As an example, collection of 500 EEG records with 'seizure' and 'non-seizure' labels in the training dataset may be considered sufficient training data to update the base model. Accordingly, different implanted neurostimulation systems 304 may provide IMD-updated models 404, 604 at different times. In any case, when the base model of a particular implanted neurostimulation systems 304 is updated, parameters of the IMD-updated model, e.g., the weights, may be sent for federated aggregation by a server 302 or subserver 306.

Replacing a Base Model

In the above described scenarios of federated learning, a pre-trained base model 402, 602 is initially provided to the implanted medical devices 304 and subsequently updated. In the first scenario of FIG. 4, the pre-trained, initial base model 402 is updated locally at the implanted medical devices 304 to an IMD-updated model 404 then remotely at a server 302 to a server-updated model 408. In the second scenario of FIG. 6A, the pre-trained, initial base model 602 is updated remotely at a subservers 306 to a subserver-updated model 608, and then remotely at a server to a server-updated model 608. In the third scenario of FIG. 6B, the pre-trained, initial base model 602 is updated locally at the implanted medical devices 304 to an IMD-updated model 604, then remotely at a subserver 306 to a subserver-updated model 608, and then remotely at a server 302 to a server-updated model 610. In the end, each of the updated machine learning models 404, 408, 604, 608, 610 have the same structure or architecture as the pre-trained initial base model 402, 602. For example, each updated machine learning model 404, 408, 604, 608, 610 may have the neural network architecture of FIG. 5.

In another embodiment, instead of updating the initial base model 402, 602 and maintaining its architecture, another type of model having a structure or architecture different from the initial base model is trained on datasets and replaces the initial base model. This other type of model is referred to herein as a new model. Depending on the complexity of the structure or architecture of the new model, the training of the new model may be done locally at the implanted medical device 304, on an external apparatus, e.g., patient monitor, remote programmer, associated with an implanted medical device, or a subserver 306 associated with a hospital. The trained new model is trained locally at the implanted medical devices 304 to an IMD-updated model 404, 604 or locally at the subservers 306 to a subserver-updated model 608, and then to a server-updated model 408, 610 by the server 302.

Figure 8B:
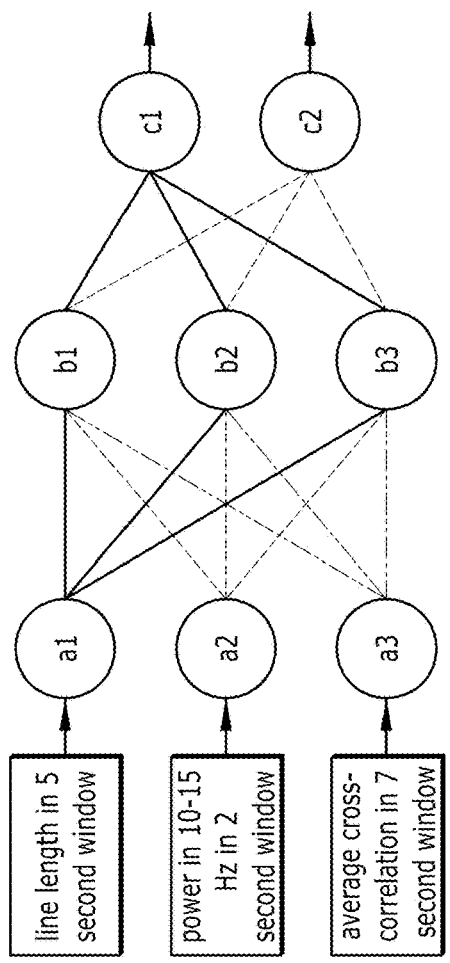
FIGS. 8A, 8B, and 8C are illustrations of different types of models that may be trained by the training system of FIG. 3.
Figure 8C:
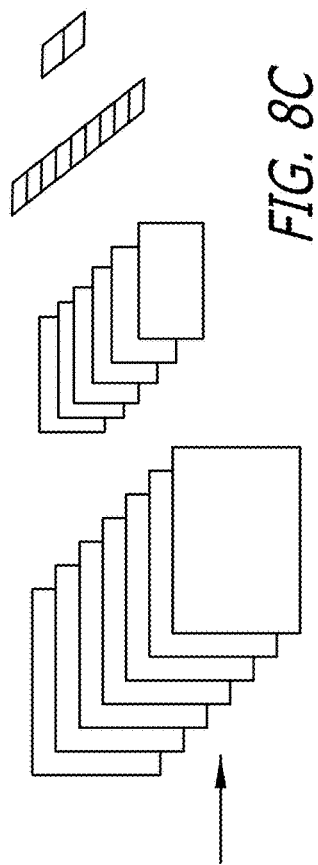
Figure 8A:
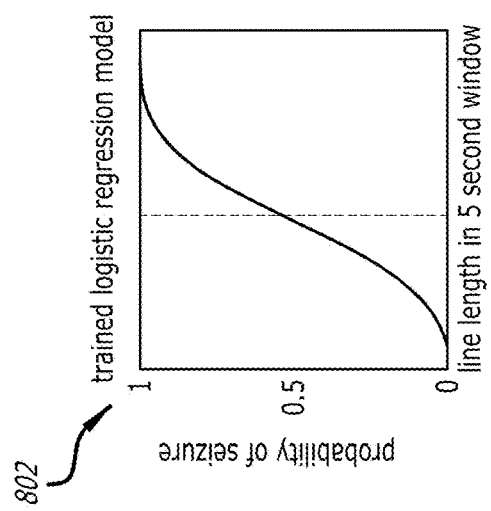

With reference to FIGS. 8A, 8B, and 8C, an initial base model provided to the implanted medical devices 304 may be a very simple logistic regression based trained base model 802. In this case, the trained base model 802 may be used by the implanted medical devices for classifying EEG signals into seizures and not seizures based on a single input feature, e.g., a line-length extracted from EEG signals. One or more new models 804, 806 having more complex architectures than the initial base model 802 may also be uploaded to the implanted medical devices 304 or subservers 306. These new models 804, 806 may be trained from scratch, either at the implanted medical device 304 level or subserver 306 level on the datasets collected by the implanted medical devices. Model replacement allows for implanted medical devices 304 to transition from using one type of model, e.g., logistic regression model 802, to another more sophisticated type of model, e.g., deep neural network 804, or convolutional neural network 806.

In some cases, depending on the architecture of the new model 804, 806, the physiological information, e.g., EEG features, that will be used for training the models may have to be specified and provided to the implanted medical device 304 or subserver 306. For example, if the new model is a decision tree or support vector based model, features such as line length, spectral power or autocorrelation and cross correlation features may be specified. Or if the new model architecture is a convolutional neural network, the length of EEG records needed for training may be specified. For example, a preferred length of EEG records may be 90 seconds or 180 seconds and may be specified for training the convolutional neural networks. Convolutional neural networks typically require inputs to be of fixed size, and hence the length of EEG records to be processed during training and testing may be specified. By maintaining flexibility regarding the architecture of the models that are used, the company may achieve better model performance and more control over model training processes. This may be beneficial from a regulatory point of view.

Regarding pre-trained base models 402, 602, these models can be based on a variety of machine learning/deep learning models such as convolutional neural networks, recurrent neural networks, random forests, decision trees, logistic regressions, support vector machines or any combination of a variety of machine/deep learning models.

Labels are generally necessary for the training of supervised machine learning algorithms. In the case of training seizure detection or prediction models based on EEG records, labels are generated and associated with the records to indicate which records represent seizures and which do not represent seizures. EEG records labeled as seizures are used for training of the machine learning models, while those labeled as non-seizures are not. As previously described, these labels may be generated and associated with an EEG record in several ways. In one example, a patient with an implanted neurostimulation system may swipe a magnet whenever he/she experiences a clinical seizure, thus triggering the creation of an EEG record, together with a "seizure" label for that EEG record. In another case, patients may maintain detailed electronic records of when they had seizures and when they did not have seizures, e.g. a seizure diary. This data is then used to identify EEG records within a dataset that contain electrographic seizures and EEG records that do not, and to label respective EEG records accordingly. In another example, 3D accelerometers in a wearable device, e.g., a smart watch, may be worn by a patient and used to generate training labels. For example, in some patients, 3D accelerometer values above a certain threshold may be strongly correlated with the patient's seizures. In such cases the seizure/not seizure labels for EEG data may be generated from the 3D accelerometer values. To this end, accelerometer data from the wearable device may be communicated to the implanted neurostimulation system and correlated in time with EEG records to assign labels. For example, EEG records captured during times when the amplitude of the accelerometer data exceeds a patient-specific value may be assigned a "seizure" label, while all other EEG records are assigned a "non-seizure" label.

With reference to FIG. 1B, as previously described EEG signals may be time stamped and labeled as being a seizure or not a seizure. Note, however, that not all EEG records stored by an implanted medical device 304 are necessarily labeled. It is possible for some EEG records to be unlabeled. For example, when using accelerometer data (as described above) for generating seizure and non-seizure labels, EEG records associated with noisy/missing accelerator data may be unlabeled. Such unlabeled EEG records may not be used for the model training process. Alternatively, if labels are only available for a small fraction of the EEG records, other methods may be used for training seizure detection and/or prediction models. For example, methods such as few-shot learning, which enables model training with just one of few labeled examples of each class (See Snell et al., "Prototypical networks for few-shot learning." Advances in neural information processing systems, pp. 4077-4087, 2017) may be used. These models may be created using a supervised training process that relies on labeled datasets.

Method of Federated Training

Figure 9A:
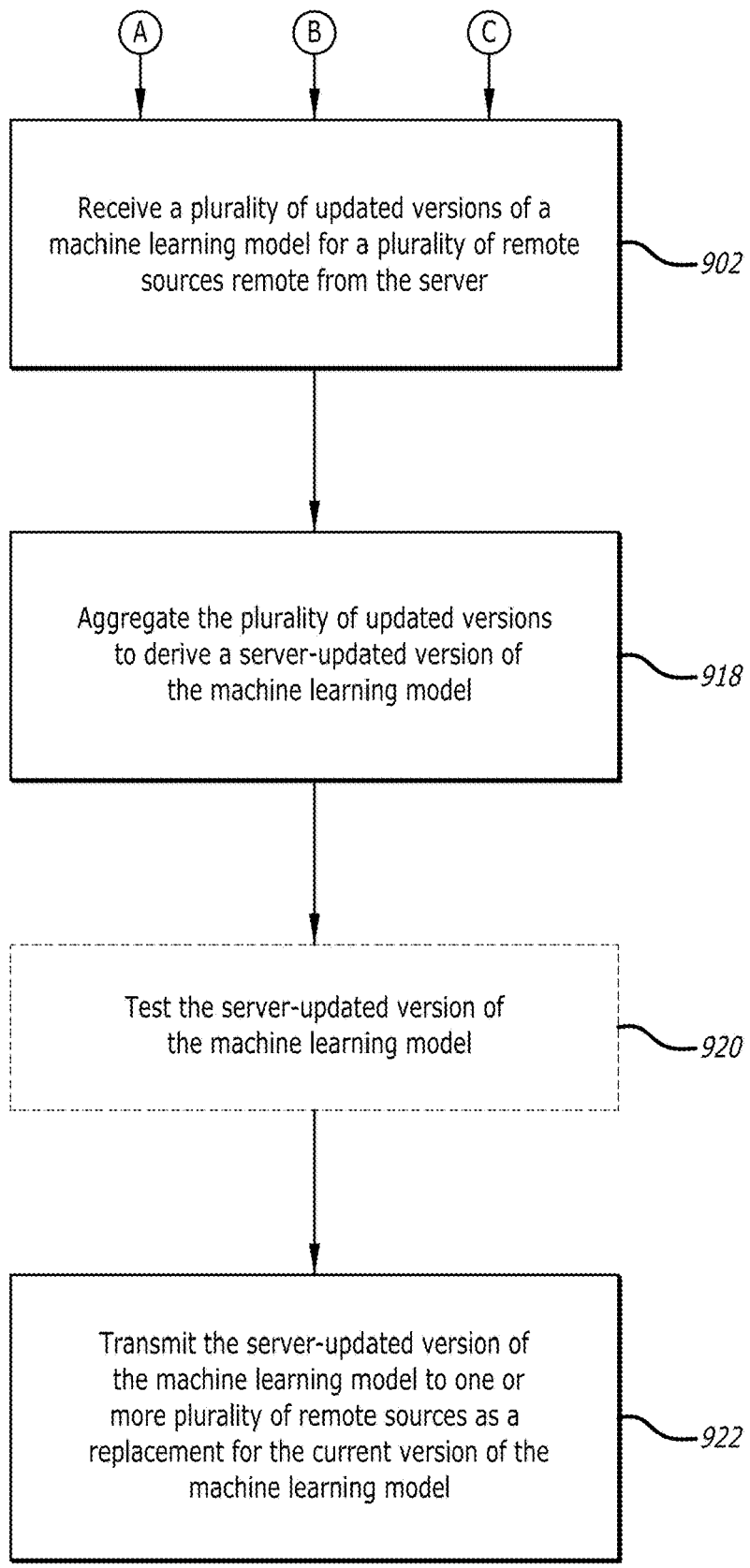
FIGS. 9A, 9B, and 9C are a flowchart of a method of updating a current version of a machine learning model resident in a number of implanted medical devices.
Figure 9B:
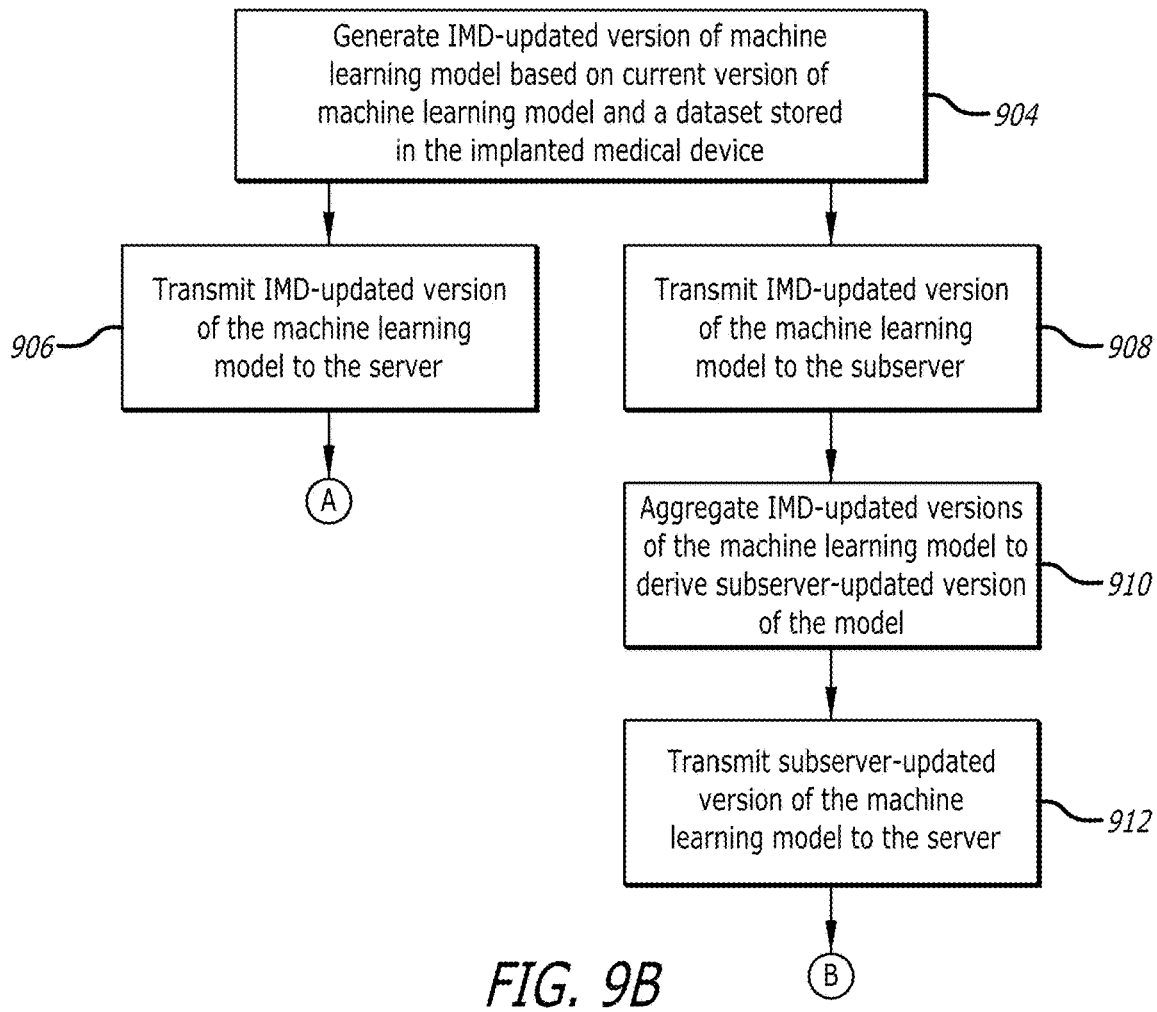
Figure 9C:
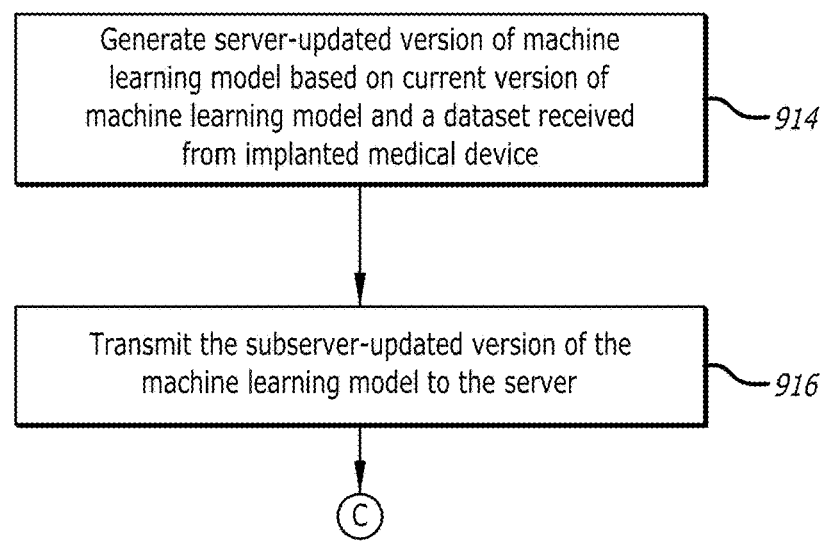

FIGS. 9A, 9B, and 9C are flowcharts of a method of updating a current version of a machine learning model resident in a plurality of implanted medical devices. Some aspects of the method, including those in FIG. 9A, may be performed by a server 302 in a training system 300, such as shown in FIGS. 3, 4, 6A, and 6B. Other aspects of the method, including those in FIGS. 9B and 9C, may be performed by an implanted medical device 304 or a subserver 306 in a training system 300.

The machine learning model may be configured to detect a neurological event, or to predict an occurrence of a neurological event, or to initiate a delivery of a stimulation therapy. In some embodiments, the machine learning model may be a neural network architecture having a plurality of nodes, wherein pairs of nodes are interconnected by a connection having an associated weight, and each node has an associated bias. In some embodiments, the machine learning model may be a logistic regression having one or more parameters, a convolutional neural network (CNN), an autoencoder or a recurrent neural network (RNN). In some embodiments, the machine learning model may be a combination of two or more of the foregoing.

With reference to FIG. 9A, at block 902, a server 302 receives a plurality of updated versions of the machine learning model 404, 608 from a plurality of remote sources 304, 306 remote from the server. The plurality of updated versions of the machine learning model 404, 608 may be received at the server synchronously or asynchronously.

With reference to FIG. 9B, in some embodiments, the updated versions of the machine learning model received by the server 302 in block 902 of FIG. 9A are IMD-updated models 404, 604 generated by one or more implanted medical devices 304. In this case, at block 904, the one or more implanted medical devices 304 generate an IMD-updated version of the machine learning model 404 based on the current version of the machine learning model and a dataset stored in the implanted medical device. Then at block 906, the one or more implanted medical devices transmit their respective IMD-updated version of the machine learning model 404 to the server 302.

Considering block 904 further, to generate IMD-updated models 404, 604 the one or more of the implanted medical devices 304 extract features from a plurality of physiological records included in the dataset, and train (or retrain) the machine learning model on the extracted features. The plurality of physiological records may be of a same type. For example, the records may all correspond to electrical activity of a brain, neural tissue motion, heart rate, blood profusion, blood oxygenation, neurotransmitter concentrations, blood glucose, sweat hormones, body motion, or pH level. In some embodiments, each of the plurality of physiological records has a same tag, which identifies a common aspect among the plurality of physiological records. The common aspect may be, for example, an occurrence of a neurological event; absence of a neurological event, and patient state.

The extracted features may be one or more of: an EEG signal characteristics (line length, power spectral density, etc.), measurements of pH level in neural tissue, measurements of blood oxygen level in neural tissue, measurements of neurotransmitters concentrations in neural tissue, measurements of heart rate, measurements of blood pressure, measurements of blood glucose levels, measurements of hormones sensed in sweat, measurements of activity based on accelerometer recordings, measurements of sleep state based on accelerometer recordings, and measurements of body position based on gyroscope recordings.

It is noted that one or more implanted medical devices 304 in a training system 300 may opt out of participation in the method of FIGS. 9A and 9B. To this end, one or more of the plurality of implanted medical devices 304 may be designated as a device that refrains from generating an IMD-updated version of the machine learning model 404, 604. Such designation may correspond to a programmable setting at the implanted medical device that causes the device to not generate IMD-updated models. This designation may also correspond to a programmable setting at the server 302 (or subserver 306) that informs the server of that a device has opted out and will not be providing IMD-updated models or datasets to the server. One or more of the plurality of implanted medical devices may also be designated as a device that refrains from receiving the server-updated version of the machine learning model. Such designation may correspond to a programmable setting at the implanted medical device that causes the device to reject any server-updated version of the machine learning model that may be transmitted to it. This designation may also correspond to a programmable setting at the server 302 (or subserver 306) that informs the server that a device has opted out and causes the server to not transmit server-updated versions of the model to that device.

With continued reference to FIG. 9B, in some embodiments the updated versions of the machine learning model received by the server 302 in block 902 of FIG. 9A are subserver-updated models 608 derived by one or more implanted medical devices 304 based on IMD-updated models 404, 604. In this case, at block 908 the one or more implanted medical devices transmit their respective IMD-updated version of the machine learning model 604 to a corresponding subserver 306 of a plurality of subservers that are remote from the server 302. At block 910, the subserver 306 aggregates the IMD-updated versions of the machine learning model to derive a subserver-updated version of the machine learning model 608. Then at block 912, the subserver 306 transmits the subserver-updated version of the machine learning model 608 to the server 302.

With reference to FIG. 9C, in some embodiments the updated versions of the machine learning model received by the server 302 in block 902 of FIG. 9A are subserver-updated models 608 trained by subservers 306 based on datasets 614 receive by the subservers from one or more implanted medical devices 304. In this case, at block 914 the one or more subservers 306 generate a subserver-updated version of the machine learning model 608 based on a dataset 614 received by the subserver from one or more of the plurality of implanted medical devices 304. At block 916, the one or more subservers 306 transmit the subserver-updated version of the machine learning model 608 to the server 302.

Considering block 914 further, in some embodiments a subserver 306 merges or pools datasets from different implanted medical devices to generate server-updated models 608. To this end, the one or more subservers 306 pool a plurality of datasets 614 received from the one or more implanted medical devices 304 to create a dataset pool. The one or more subservers 306 then training the current version of the machine learning model on the dataset pool. Training may include extracting, at the one or more subservers, features from a plurality of physiological records; and training the machine learning model on the extracted features.

Considering block 914 further, in some embodiments instead of pooling datasets, the subservers 306 processes each dataset separately to derive individual updated models and then combines the models. To this end, for each of the one or more of the implanted medical devices 304 from which a subserver 306 receives a dataset 614, the subservers 306 trains the current version of the machine learning model on the dataset 614 to derive an IMD-updated version of the machine learning model, and then aggregates the IMD-updated versions to derive the subserver-updated version of the machine learning model.

Returning to FIG. 9A, at block 918, the server 302 aggregates the plurality of updated versions to derive a server-updated version of the machine learning model 408, 610. For example, the machine learning model may be a neural network architecture 500 having a plurality of nodes. The neural network architecture 500 is characterized by a plurality of biases, wherein each of the plurality of biases is associated with a corresponding node of the plurality of nodes. In this embodiment, aggregating the plurality of updated versions of the machine learning model 404, 604, 608 includes: for a particular node of the plurality of nodes included in the updated versions of the machine learning model, calculating an average of the biases associated with that particular node, and assigning the average to the at least one node. Aggregating the plurality of updated versions of the machine learning model 404, 604, 608 may further include: prior to calculating an average of the biases, applying a weight factor to each of the biases associated with the particular node. The applied weight factor is based on an amount of data included in a dataset on which the updated version of the machine learning model was trained.

In another example, the machine learning model may be a neural network architecture 500 having a plurality of nodes and a plurality of interconnections between pair of nodes of the plurality of nodes. The neural network architecture 500 is characterized by a plurality of weights, wherein each weight of the plurality of weights is associated with a corresponding one of the plurality of interconnections. In this embodiment, aggregating the plurality of updated versions of the machine learning model 404, 604, 608 includes: for at least one connection of the plurality of interconnection included in the plurality of updated versions, calculating an average of the weights associated with the at least one interconnection, and assigning the average to the at least one interconnection. Aggregating the plurality of updated versions of the machine learning model 404, 604, 608 may further include: prior to calculating an average of the weights, applying a weight factor to each of the weights associated with the at least one interconnection. The applied weight factor is based on an amount of data included in a dataset on which the updated version of the machine learning model was trained.

In another example, the machine learning model may be a neural network architecture 500 having a plurality of nodes. The neural network architecture 500 is characterized by a plurality of biases, wherein each of the plurality of biases is associated with a corresponding node of the plurality of nodes. In this embodiment, aggregating the plurality of updated versions of the machine learning model 404, 604, 608 includes: grouping the plurality of nodes into one or more sets of nodes based on one of probabilistic federated neural matching or federated matched averaging; for at least one of the sets of nodes, calculating an average of the biases associated with the set of nodes, and assigning the average to the nodes included in the set of nodes.

At optional block 920, the server 302 tests the server-updated version of the machine learning model prior to transmitting the server-updated version of the machine learning model to one or more of the plurality of remote sources. For example, the server 302 may be configured to test the server-updated model 408 on test data, which may be simulated, or real patient data. If performance of the server-updated model 408 is worse than the performance of the base model 402 the server 302 may reject the server-update model.

At block 922, the server 302 transmits the server-updated version of the machine learning model 408, 610 to one or more of the plurality of remote sources 304, 306 as a replacement for the current version of the machine learning model.

Having thus described the configuration and operation of a training system 300, an overview of an example implanted neurostimulation system that may be included in the system is provided.

Overview of Implanted Neurostimulation System

Figure 10:
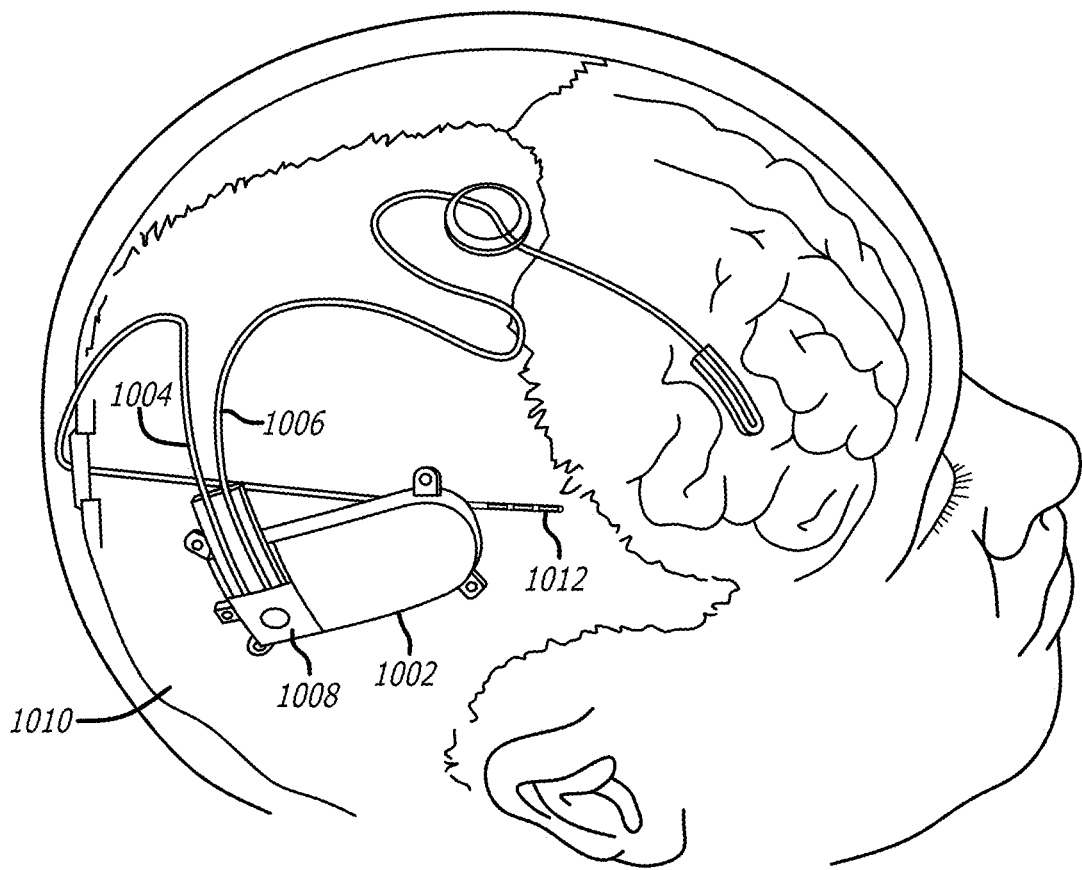
FIG. 10 is a perspective, schematic illustration of a neurostimulation system implanted in a patient and configured to sense and record EEG records and other physiological information used by the system of FIG. 3.

FIG. 10 is an illustration of the implanted neurostimulation system including an active neurostimulator 1002 and two electrode-bearing brain leads 1004, 1006, implanted in a patient. The system is configured to sense and record electrical brain activity and other physiological information to be used by the training system of FIG. 3.

The neurostimulator 1002 includes a lead connector 1008 adapted to receive one or more of the brain leads, such as a deep brain or depth lead 1004 and a cortical strip lead 1006. The depth lead is implanted so that a distal end of it is situated within the patient's neural tissue, whereas the cortical strip lead is implanted under the dura mater so that a distal end of it rests on a surface of the brain. The lead connector 1008 acts to physically secure the brain leads 1004, 1006 to the neurostimulator 1002, and facilitates electrical connection to conductors in the brain leads 1004, 1006 coupling one or more electrodes at or near a distal end of the lead to circuitry within the neurostimulator 1002.

The proximal portion of the deep brain lead 1004 is generally situated on the outer surface of the cranium 1010 (and under the patient's scalp), while the distal portion of the lead enters the cranium 1010 and is coupled to at least one depth electrode 1012 implanted in a desired location in the patient's brain. The proximal portion of the cortical lead 1006 is generally situated on the outer surface of the cranium 1010 (and under the patient's scalp), while the distal portion of the lead enters the cranium 1010. The distal portion of the cortical lead 1006 includes at least one cortical electrode (not visible) implanted in a desired location on the patient's brain.

Figure 11:
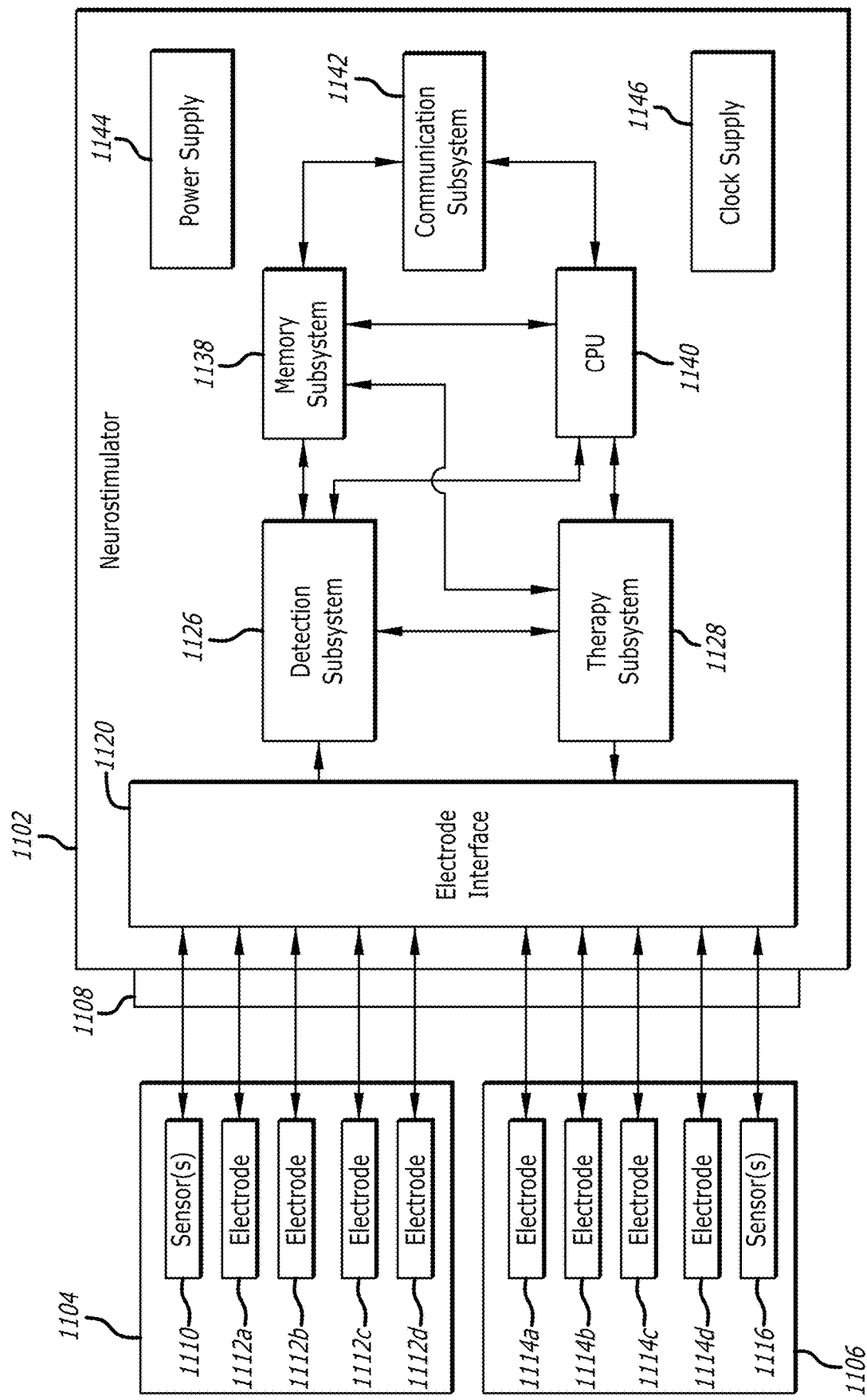
FIG. 11 is a block diagram of the implanted neurostimulation system of FIG. 10, illustrating some of the functional subsystems of the system.

FIG. 11 is a block diagram of the implanted neuro stimulation system of FIG. 11 The system may be configured to sense electrical brain activity, detect neurological events in accordance with a set of detection parameters, delivery electrical neurostimulation to the brain in accordance with a set of stimulation parameters, and store records of electrical brain activity and other physiological information for use by the training system of FIG. 3.

The neurostimulator 1102 includes a lead connector 1108 adapted to receive a connector end of each brain lead 1104, 1106, to thereby electrically couple each lead and its associated electrodes 1112a-d, 1114a-d with the neurostimulator. The neurostimulator 1102 may configure an electrode 1112a-d, 1114a-d as either a sensor (for purposes of sensing electrical activity of the brain) or a stimulator (for purposes of delivering therapy to the patient in the form of electrical stimulation) or both.

The electrodes 1112a-d, 1114a-d are connected to an electrode interface 1120. The electrode interface 1120 can select each electrode 1112a-d, 1114a-d as required for sensing and stimulation. The electrode interface 1120 may also provide any other features, capabilities, or aspects, including but not limited to, amplification, isolation, and charge-balancing functions, that are required for a proper interface with neurological tissue. The electrode interface 1120 is coupled to a detection subsystem 1126, which is configured to process electrical activity of the brain sensed through the electrode 1112a-d, 1114a-d. The electrode interface 1120 may also be coupled to a therapy subsystem 1128, which is configured to deliver therapy to the patient through the electrode 1112a-d, 1114a-d in the form of electrical stimulation.

One or both of the brain leads 1104, 1106 may have one or more physiological sensors 1110, 1116 that enable the capture and recording of other types of physiological information, e.g., pH levels, blood oxygen levels, neurotransmitters concentrations, heart rate, blood pressure, blood glucose levels, hormone levels, sleep states, posture, etc. To this end, one or both of the brain leads 1104, 1106 may be configured as disclosed in U.S. Pat. No. 10,123,717, entitled Multi-modal Brain Sensing Lead, which is herein incorporated by reference, and the one or more physiological sensors 1110, 1116 may correspond to different transducers, e.g., macro-electrodes, microelectrodes, light emitters, and photodetectors that enable different sensing modalities.

The neurostimulator 1102 includes a memory subsystem 1138 and a central processing unit (CPU) 1140, which can take the form of a microcontroller. The memory subsystem 1138 is coupled to the detection subsystem 1126, and may receive and store records of data representative of sensed electrographic signals. The memory subsystem 1138 is also coupled to the therapy subsystem 1128 and the CPU 1140. In addition to the memory subsystem 1138, the CPU 1140 is also connected to the detection subsystem 1126 and the therapy subsystem 1128 for direct control of those subsystems.

The neurostimulator 1102 also includes a communication subsystem 1142. The communication subsystem 1142 enables communication between the neurostimulator 1102 and an external device, such as a programmer 116 or patient monitor 110, through a wireless communication link. As described above with reference to FIG. 1, the programmer 116 allows a clinician to read out records of patient data, as well as ancillary information associated with those records. The neurostimulator 1102 also includes a power supply 1144 and a clock supply 1146. The power supply 1144 supplies the voltages and currents necessary for each of the other subsystems. The clock supply 1146 supplies substantially all the other subsystems with any clock and timing signals necessary for their operation.

Server

Figure 12:
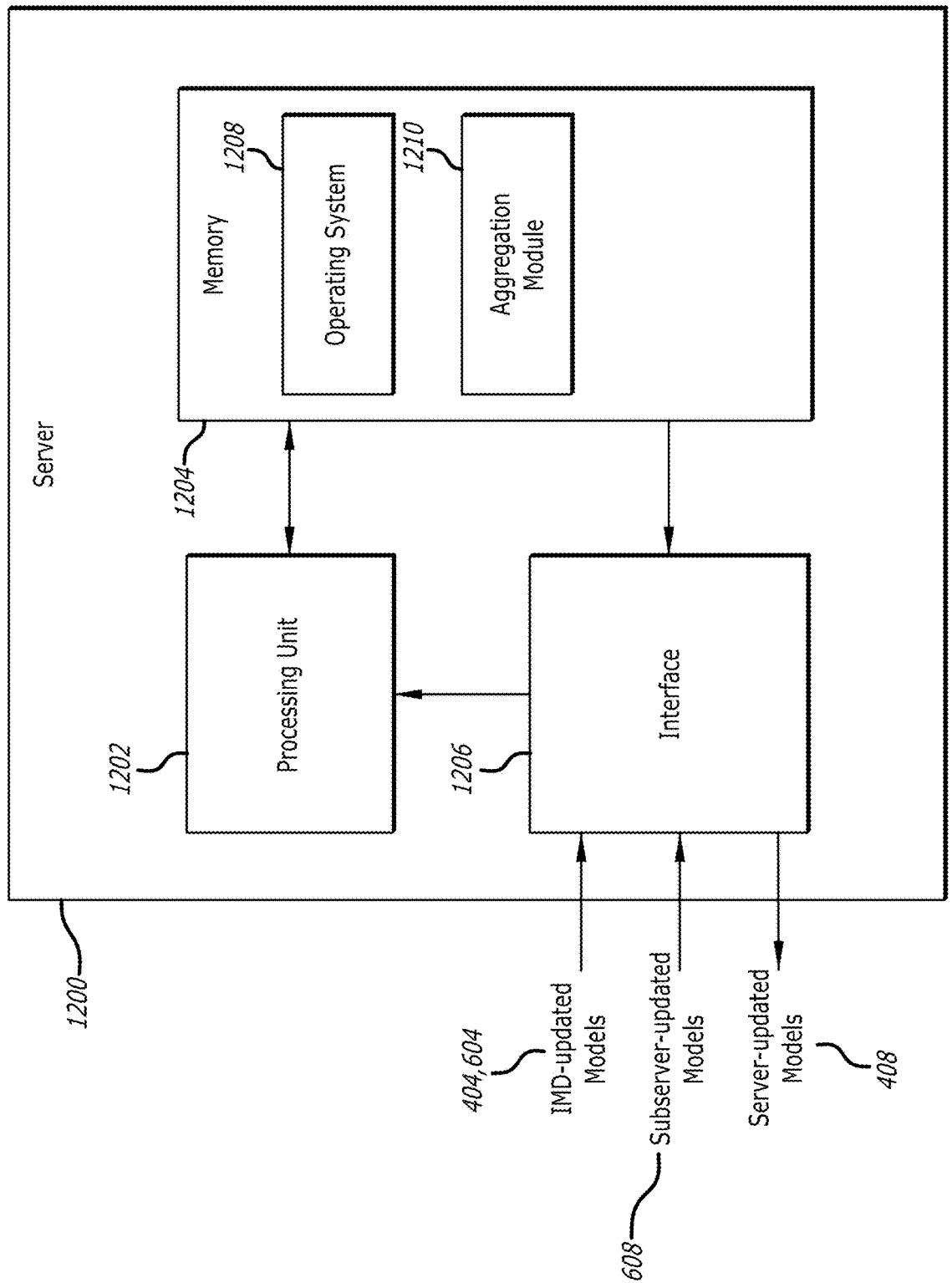
FIG. 12 is a block diagram of a server in the training system of FIG. 3.

FIG. 12 is a schematic block diagram of an apparatus 1200 corresponding to the server 302 of FIGS. 3, 4, 6A, and 6B. The apparatus 1200 is configured to execute instructions related to the model update processes described above with reference to FIGS. 4, 6A, 6B, and 9. The apparatus 1200 may be embodied in any number of processor-driven devices, including, but not limited to, a server computer, a personal computer, one or more networked computing devices, an application-specific circuit, a minicomputer, a microcontroller, and/or any other processor-based device and/or combination of devices.

The apparatus 1200 may include one or more processing units 1202 configured to access and execute computer-executable instructions stored in at least one memory 1204. The processing unit 1202 may be implemented as appropriate in hardware, software, firmware, or combinations thereof. Software or firmware implementations of the processing unit 1202 may include computer-executable or machine-executable instructions written in any suitable programming language to perform the various functions described herein. The processing unit 1502 may include, without limitation, a central processing unit (CPU), a digital signal processor (DSP), a reduced instruction set computer (RISC) processor, a complex instruction set computer (CISC) processor, a microprocessor, a microcontroller, a field programmable gate array (FPGA), a System-on-a-Chip (SOC), or any combination thereof. The apparatus 1200 may also include a chipset (not shown) for controlling communications between the processing unit 1202 and one or more of the other components of the apparatus 1200. The processing unit 1202 may also include one or more application-specific integrated circuits (ASICs) or application-specific standard products (ASSPs) for handling specific data processing functions or tasks.

The memory 1204 may include, but is not limited to, random access memory (RAM), flash RAM, magnetic media storage, optical media storage, and so forth. The memory 1204 may include volatile memory configured to store information when supplied with power and/or non-volatile memory configured to store information even when not supplied with power. The memory 1204 may store various program modules, application programs, and so forth that may include computer-executable instructions that upon execution by the processing unit 1202 may cause various operations to be performed. The memory 1204 may further store a variety of data manipulated and/or generated during execution of computer-executable instructions by the processing unit 1202.

The apparatus 1200 may further include one or more interfaces 1206 that facilitate communication between the apparatus and one or more other apparatuses. For example, the interface 1206 may be configured to receive IMD-update models 404, 604 from implanted medical devices 304 and subserver-updated models 608 from subserver 306. The interface 1206 is also configured to transmit or send server-updated models 408, 608 to implanted medical devices 304 or subservers 306. Communication may be implemented using any suitable communications standard. For example, a LAN interface may implement protocols and/or algorithms that comply with various communication standards of the Institute of Electrical and Electronics Engineers (IEEE), such as IEEE 802.11.

The memory 1204 may store various program modules, application programs, and so forth that may include computer-executable instructions that upon execution by the processing unit 1202 may cause various operations to be performed. For example, the memory 1204 may include an operating system module (O/S) 1208 that may be configured to manage hardware resources such as the interface 1206 and provide various services to applications executing on the apparatus 1200.

The memory 1204 stores additional program modules such as an aggregation module 1210 that aggregates the IMD-update models 404, 604 received from implanted medical devices 304 and the subserver-updated models 608 received from subservers 306 to derive a server-updated version of the machine learning model 408, 610. This module 1210 includes computer-executable instructions that when executed by the processing unit 1202 cause various operations to be performed, such as the operations described immediately above and earlier with reference to FIGS. 4, 6A, 6B, and 9.

The apparatus 1200 and modules disclosed herein may be implemented in hardware or software that is executed on a hardware platform. The hardware or hardware platform may be a general purpose processor, a digital signal processor (DSP), an application specific integrated circuit (ASIC), a field programmable gate array (FPGA) or other programmable logic component, discrete gate or transistor logic, discrete hardware components, or any combination thereof, or any other suitable component designed to perform the functions described herein. A general-purpose processor may be a microprocessor, but in the alternative, the processor may be any conventional processor, controller, microcontroller, or state machine. A processor may also be implemented as a combination of computing components, e.g., a combination of a DSP and a microprocessor, a plurality of microprocessors, one or more microprocessors in conjunction with a DSP, or any other such configuration.

Subserver

Figure 13:
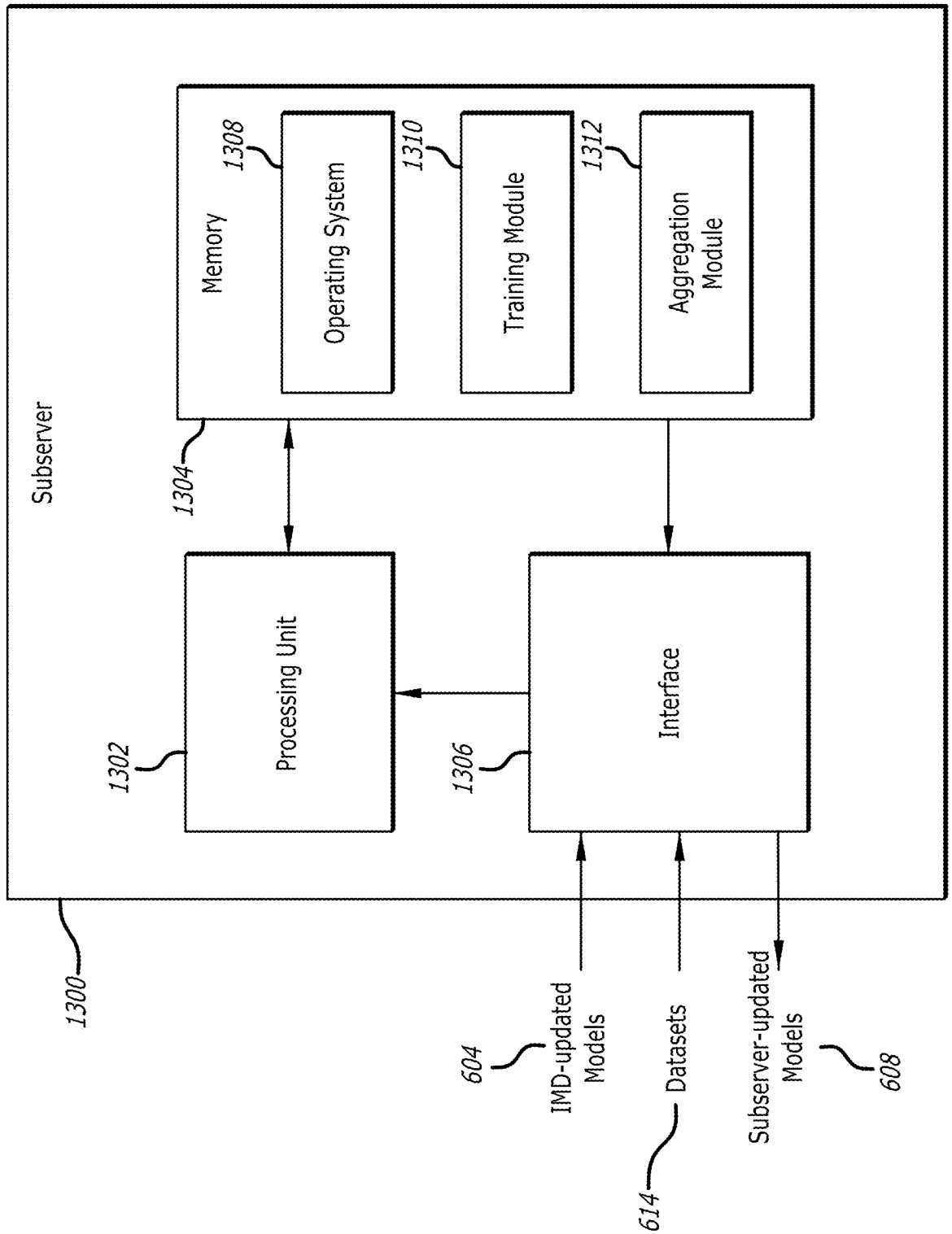
FIG. 13 is a block diagram of a subserver in the training system of FIG. 3.

FIG. 13 is a schematic block diagram of an apparatus 1300 corresponding to the subserver 306 of FIGS. 3, 4, 6A, and 6B. The apparatus 1300 is configured to execute instructions related to the model update processes described above with reference to FIGS. 4, 6A, 6B, and 9. The apparatus 1300 may be embodied in any number of processor-driven devices, including, but not limited to, a server computer, a personal computer, one or more networked computing devices, an application-specific circuit, a minicomputer, a microcontroller, and/or any other processor-based device and/or combination of devices.

The apparatus 1300 may include one or more processing units 1302 configured to access and execute computer-executable instructions stored in at least one memory 1304. The processing unit 1302 may be implemented as appropriate in hardware, software, firmware, or combinations thereof. Software or firmware implementations of the processing unit 1302 may include computer-executable or machine-executable instructions written in any suitable programming language to perform the various functions described herein. The processing unit 1302 may include, without limitation, a central processing unit (CPU), a digital signal processor (DSP), a reduced instruction set computer (RISC) processor, a complex instruction set computer (CISC) processor, a microprocessor, a microcontroller, a field programmable gate array (FPGA), a System-on-a-Chip (SOC), or any combination thereof. The apparatus 1300 may also include a chipset (not shown) for controlling communications between the processing unit 1302 and one or more of the other components of the apparatus 1300. The processing unit 1302 may also include one or more application-specific integrated circuits (ASICs) or application-specific standard products (ASSPs) for handling specific data processing functions or tasks.

The memory 1304 may include, but is not limited to, random access memory (RAM), flash RAM, magnetic media storage, optical media storage, and so forth. The memory 1304 may include volatile memory configured to store information when supplied with power and/or non-volatile memory configured to store information even when not supplied with power. The memory 1304 may store various program modules, application programs, and so forth that may include computer-executable instructions that upon execution by the processing unit 1302 may cause various operations to be performed. The memory 1304 may further store a variety of data manipulated and/or generated during execution of computer-executable instructions by the processing unit 1302.

The apparatus 1300 may further include one or more interfaces 1306 that may facilitate communication between the apparatus and one or more other apparatuses. For example, the interface 1306 may be configured to receive IMD-update models 604 and datasets 614 from implanted medical devices 304. The interface 1306 is also configured to transmit or send subserver-updated models 608 to a server 302. Communication may be implemented using any suitable communications standard. For example, a LAN interface may implement protocols and/or algorithms that comply with various communication standards of the Institute of Electrical and Electronics Engineers (IEEE), such as IEEE 802.11.

The memory 1304 may store various program modules, application programs, and so forth that may include computer-executable instructions that upon execution by the processing unit 1302 may cause various operations to be performed. For example, the memory 1304 may include an operating system module (O/S) 1308 that may be configured to manage hardware resources such as the interface 1306 and provide various services to applications executing on the apparatus 1300.

The memory 1304 stores additional program modules such as a training module 1310 that updates a current version of a model into a subserver-updated model 608 using datasets 614 received from implanted medical device 304; and an aggregation module 1312 that aggregates the IMD-update models 404, 604 received from implanted medical devices 304 to derive a subserver-updated version 608 of the machine learning model. These modules 1310, 1312 includes computer-executable instructions that when executed by the processing unit 1302 cause various operations to be performed, such as the operations described immediately above and earlier with reference to FIGS. 4, 6A, 6B, and 9.

The apparatus 1300 and modules disclosed herein may be implemented in hardware or software that is executed on a hardware platform. The hardware or hardware platform may be a general purpose processor, a digital signal processor (DSP), an application specific integrated circuit (ASIC), a field programmable gate array (FPGA) or other programmable logic component, discrete gate or transistor logic, discrete hardware components, or any combination thereof, or any other suitable component designed to perform the functions described herein. A general-purpose processor may be a microprocessor, but in the alternative, the processor may be any conventional processor, controller, microcontroller, or state machine. A processor may also be implemented as a combination of computing components, e.g., a combination of a DSP and a microprocessor, a plurality of microprocessors, one or more microprocessors in conjunction with a DSP, or any other such configuration.

Implanted Medical Device

Figure 14:
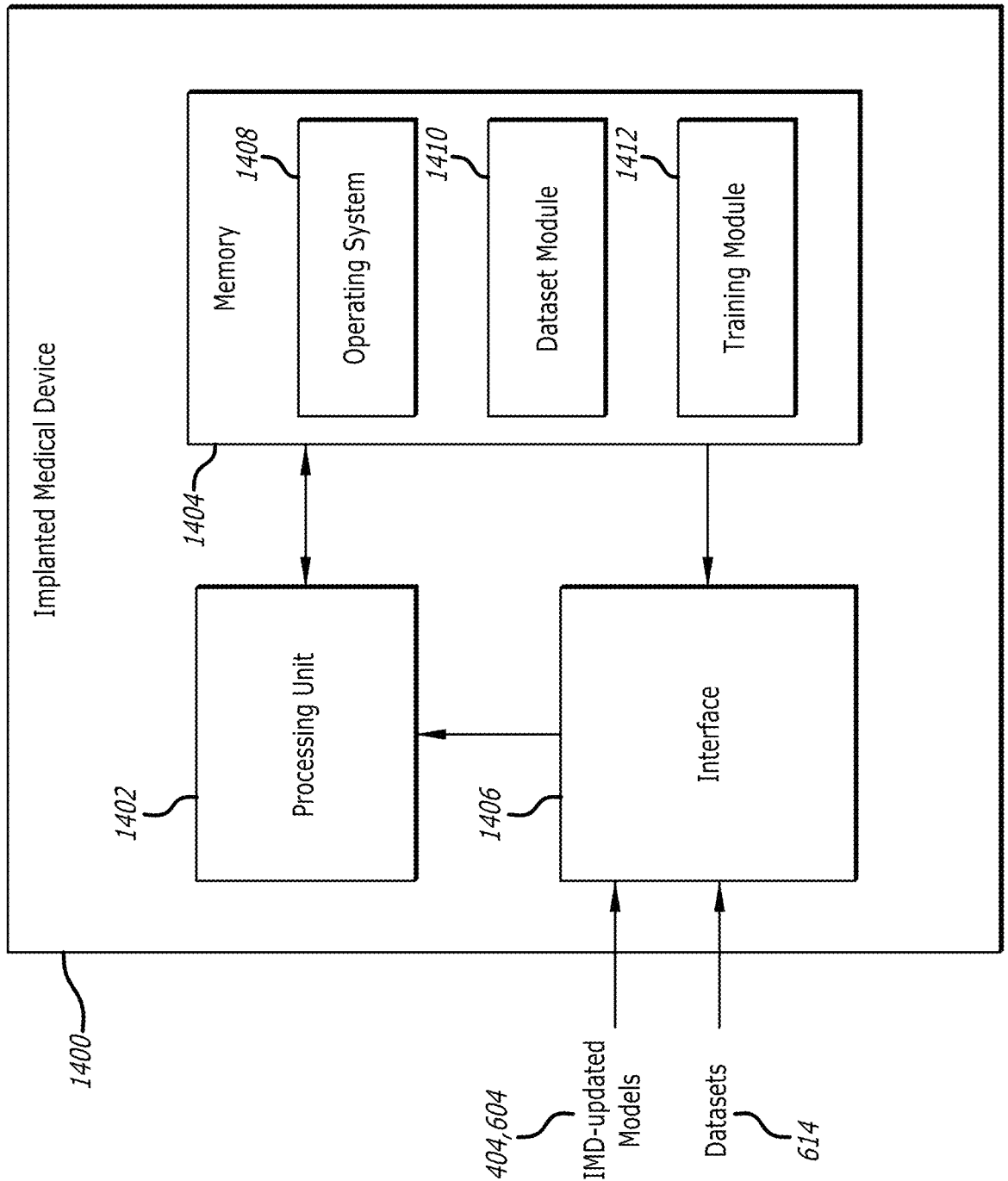
FIG. 14 is a block diagram of an implanted medical device in the training system of FIG. 3.

FIG. 14 is a schematic block diagram of an apparatus 1400 corresponding to an implanted medical device 304 of FIGS. 3, 4, 6A, and 6B. The apparatus 1400 is configured to execute instructions related to the model update processes described above with reference to FIGS. 4, 6A, 6B, and 9. The apparatus 1400 may be embodied in any number of processor-driven devices, including, but not limited to, a server computer, a personal computer, one or more networked computing devices, an application-specific circuit, a minicomputer, a microcontroller, and/or any other processor-based device and/or combination of devices.

The apparatus 1400 may include one or more processing units 1402 configured to access and execute computer-executable instructions stored in at least one memory 1404. The processing unit 1402 may be implemented as appropriate in hardware, software, firmware, or combinations thereof. Software or firmware implementations of the processing unit 1402 may include computer-executable or machine-executable instructions written in any suitable programming language to perform the various functions described herein. The processing unit 1402 may include, without limitation, a central processing unit (CPU), a digital signal processor (DSP), a reduced instruction set computer (RISC) processor, a complex instruction set computer (CISC) processor, a microprocessor, a microcontroller, a field programmable gate array (FPGA), a System-on-a-Chip (SOC), or any combination thereof. The apparatus 1400 may also include a chipset (not shown) for controlling communications between the processing unit 1402 and one or more of the other components of the apparatus 1400. The processing unit 1402 may also include one or more application-specific integrated circuits (ASICs) or application-specific standard products (ASSPs) for handling specific data processing functions or tasks.

The memory 1404 may include, but is not limited to, random access memory (RAM), flash RAM, magnetic media storage, optical media storage, and so forth. The memory 1404 may include volatile memory configured to store information when supplied with power and/or non-volatile memory configured to store information even when not supplied with power. The memory 1404 may store various program modules, application programs, and so forth that may include computer-executable instructions that upon execution by the processing unit 1402 may cause various operations to be performed. The memory 1404 may further store a variety of data manipulated and/or generated during execution of computer-executable instructions by the processing unit 1402.

The apparatus 1400 may further include one or more interfaces 1406 that may facilitate communication between the apparatus and one or more other apparatuses. For example, the interface 1406 may be configured to transmit or send IMD-updated models 404, 604 to a server 302 or a subserver 306, and datasets 614 to a subserver 306. Communication may be implemented using any suitable communications standard. For example, a LAN interface may implement protocols and/or algorithms that comply with various communication standards of the Institute of Electrical and Electronics Engineers (IEEE), such as IEEE 802.11.

The memory 1404 may store various program modules, application programs, and so forth that may include computer-executable instructions that upon execution by the processing unit 1402 may cause various operations to be performed. For example, the memory 1404 may include an operating system module (O/S) 1408 that may be configured to manage hardware resources such as the interface 1406 and provide various services to applications executing on the apparatus 1400.

The memory 1404 stores additional program modules such as a dataset module 1410 that collects and stores a dataset that includes physiological information of the patient in which the device is implanted; and a training module 1412 that updates a current version of a model into an IMD-updated model 404, 604 using the dataset collected by the implanted medical device 304 and stored in the dataset module 1410. These modules 1410, 1412 includes computer-executable instructions that when executed by the processing unit 1402 cause various operations to be performed, such as the operations described immediately above and earlier with reference to FIGS. 4, 6A, 6B, and 9.

The apparatus 1400 and modules disclosed herein may be implemented in hardware or software that is executed on a hardware platform. The hardware or hardware platform may be a general purpose processor, a digital signal processor (DSP), an application specific integrated circuit (ASIC), a field programmable gate array (FPGA) or other programmable logic component, discrete gate or transistor logic, discrete hardware components, or any combination thereof, or any other suitable component designed to perform the functions described herein. A general-purpose processor may be a microprocessor, but in the alternative, the processor may be any conventional processor, controller, microcontroller, or state machine. A processor may also be implemented as a combination of computing components, e.g., a combination of a DSP and a microprocessor, a plurality of microprocessors, one or more microprocessors in conjunction with a DSP, or any other such configuration.

The various aspects of this disclosure are provided to enable one of ordinary skill in the art to practice the present invention. Various modifications to exemplary embodiments presented throughout this disclosure will be readily apparent to those skilled in the art, and the concepts disclosed herein may be extended to other magnetic storage devices. Thus, the claims are not intended to be limited to the various aspects of this disclosure, but are to be accorded the full scope consistent with the language of the claims. All structural and functional equivalents to the various components of the exemplary embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A method of replacing a first machine learning model of a first architecture resident in a plurality of implanted medical devices, wherein the first machine learning model is generated using a first dataset and is configured to detect a neurological event in electrical activity of a brain, the method comprising:
providing, from a server to each of a plurality of remote sources remote from the server, information on a second dataset for generating a second machine learning model of a second architecture different than the first architecture, which second dataset includes at least one type of data that is not included in the first dataset and comprises records of electrical activity collected in response to detections of neurological events by the first machine learning model;

generating, at each of the plurality of remote sources, a version of the second machine learning model based on a corresponding second dataset;

receiving, at a server, a plurality of versions of the second machine learning model from the plurality of remote sources;

aggregating, at the server, the plurality of versions of the second machine learning model to derive a server-generated version of the second machine learning model; and transmitting, at the server, the server-generated version of the second machine learning model to one or more of the plurality of remote sources as a replacement for the first machine learning model.

2. The method of claim 1, wherein:
the second machine learning model comprises a neural network architecture having a plurality of nodes, and is characterized by a plurality of biases, each of the plurality of biases being associated with a corresponding node of the plurality of nodes, and
aggregating the plurality of versions of the second machine learning model comprises:
for at least one node of the plurality of nodes included in the plurality of versions of the second machine learning model, calculating an average of the biases associated with the at least one node, and
assigning the average to the at least one node.

3. The method of claim 2, wherein aggregating the plurality of versions of the second machine learning model further comprises:
prior to calculating an average of the biases, applying a weight factor to each of the biases associated with the at least one node, wherein each weight factor is based on an amount of data included in the second dataset on which the version of the second machine learning model was trained.

4. The method of claim 1, wherein:
the second machine learning model comprises a neural network architecture having a plurality of nodes and a plurality of interconnections between pair of nodes of the plurality of nodes, and is characterized by a plurality of weights, each weight of the plurality of weights being associated with a corresponding one of the plurality of interconnections, and
aggregating the plurality of versions of the second machine learning model comprises:
for at least one interconnection of the plurality of interconnections included in the plurality of versions of the second machine learning model, calculating an average of the weights associated with the at least one interconnection, and
assigning the average to the at least one interconnection.

5. The method of claim 4, wherein aggregating the plurality of versions of the second machine learning model further comprises:
prior to calculating an average of the weights, applying a weight factor to each of the weights associated with the at least one interconnection, wherein each weight factor is based on an amount of data included in the second dataset on which the version of the second machine learning model was trained.

6. The method of claim 1, wherein:
the second machine learning model comprises a neural network architecture having a plurality of nodes, and is characterized by a plurality of biases, each of the plurality of biases being associated with a corresponding node of the plurality of nodes, and
aggregating the plurality of versions of the second machine learning model comprises:
grouping the plurality of nodes into one or more sets of nodes based on one of probabilistic federated neural matching or federated matched averaging;
for at least one of the sets of nodes, calculating an average of the biases associated with the nodes in the at least one set of nodes; and
assigning the average to the nodes included in the at least one set of nodes.

7. The method of claim 1, wherein:
the first machine learning model comprises a logistic regression having one or more parameters; and
the second machine learning model comprises one of a convolutional neural network (CNN); an autoencoder; and a recurrent neural network (RNN).

8. The method of claim 1, wherein:
the plurality of remote sources comprises at least two of the plurality of implanted medical devices (IMD), and
the version of the second machine learning model generated by the at least two of the plurality of implanted medical devices is based on a second dataset stored in the respective implanted medical device.

9. The method of claim 8, wherein generating a version of the second machine learning model comprises:
extracting features from a plurality of physiological records included in the second dataset; and
training the version of the second machine learning model on the extracted features.

10. The method of claim 9, wherein each of the plurality of physiological records comprises:
electrical activity of a brain, and
at least one of neural tissue motion, heart rate, blood profusion, blood oxygenation, neurotransmitter concentrations, blood glucose, sweat hormones, body motion, and pH level.

11. The method of claim 9, wherein each of the plurality of physiological records has a same tag, which identifies a common aspect among the plurality of physiological records, the common aspect corresponding to one of:
an occurrence of a neurological event;
absence of a neurological event; and
patient state.

12. The method of claim 8, further comprising transmitting, at the at least two of the plurality of implanted medical devices, the IMD-generated version of the second machine learning model to the server.

13. The method of claim 8, further comprising:
transmitting, at the at least two of the plurality of implanted medical devices, the IMD-generated version of the second machine learning model to a subserver remote from the server;
aggregating, at the subserver, the IMD-generated versions to derive a subserver-generated version of the second machine learning model; and
transmitting, at the one or more subservers, the subserver-generated version of the second machine learning model to the server, wherein the subserver-generated version corresponds to one of the plurality of versions of the second machine learning model aggregated at the server.

14. The method of claim 1, wherein:
the plurality of remote sources comprises one or more subservers remote from the server,
the version of the second machine learning model generated by the one or more subservers is based on a second dataset received by the respective subserver from one or more of the plurality of implanted medical devices; and
and further comprising, transmitting, at the one or more subservers, the subserver-generated version of the second machine learning model to the server, wherein the subserver-generated version corresponds to one of the plurality of versions of the second machine learning model aggregated at the server.

15. The method of claim 14, wherein generating a subserver-generated version comprises:
pooling, at the one or more subservers, a plurality of second datasets received from the one or more of the plurality of implanted medical devices to create a dataset pool; and
training, at the one or more subservers, the version of the second machine learning model on the dataset pool.

16. The method of claim 15, wherein training comprises:
extracting, at the one or more subservers, features from a plurality of physiological records; and
training the version of the second machine learning model on the extracted features.

17. The method of claim 14, wherein generating a subserver-generated version comprises:
for one or more of the implanted medical devices from which the one or more subservers receives a second dataset:
training, at the one or more subservers, the version of the second machine learning model on the second dataset to derive a version of the second machine learning model; and
aggregating, at the one or more subservers, the versions of the second machine learning model to derive the subserver-generated version of the second machine learning model.

18. The method of claim 14, further comprising, at one or more of the plurality of implanted medical devices:
refraining from generating an IMD-generated version of the second machine learning model; and
refraining from receiving the subserver-generated version of the second machine learning model.

19. The method of claim 1, further comprising:
testing the subserver-generated version of the second machine learning model prior to transmitting the subserver-generated version of the second machine learning model to one or more of the plurality of remote sources.

20. The method of claim 1, wherein the plurality of versions of the second machine learning model is received at the server synchronously.

21. The method of claim 1, wherein the plurality of versions of the second machine learning model is received at the server asynchronously.

22. A server for replacing a first machine learning model of a first architecture resident in a plurality of implanted medical devices, wherein the first machine learning model is generated using a first dataset and is configured to detect a neurological event in electrical activity of a brain, the server comprising:
an interface configured to receive a plurality of versions of a second machine learning model from a plurality of remote sources remote from the server;
a memory; and
a processor coupled to the memory and the interface and configured to:
provide to each of the plurality of remote sources remote from the server, information on a second dataset for generating a second machine learning model of a second architecture different than the first architecture, which second dataset includes at least one type of data that is not included in the first dataset and comprises records of electrical activity collected in response to detections of neurological events by the first machine learning model;
aggregate the plurality of versions of the second machine learning model to derive a server-generated version of the second machine learning model; and
transmit the server-generated version of the second machine learning model to one or more of the plurality of remote sources as a replacement for the first machine learning model.

23. The method of claim 1, wherein the at least one type of data that is included in the second dataset but not in the first dataset comprises at least one of spectral power, an autocorrelation feature, a cross correlation feature, and a specified duration of a record of electrical activity.

24. An implantable medical device, comprising:
a first machine learning model of a first architecture, wherein the first machine learning model is generated using a first dataset and is configured to detect a neurological event in electrical activity of a brain;
an interface configured to:
receive information on a second dataset, which second dataset includes at least one type of data that is not included in the first dataset and comprises records of electrical activity collected in response to detections of neurological events by the first machine learning model, and
provide to a server, a version of a second machine learning model;
a memory storing data; and
a processor coupled to the memory and the interface and configured to:
extract the second dataset from the data stored i memory, and
generate the version of the second machine learning model based on the second dataset, wherein the second machine learning model is of a second architecture different than the first architecture.

25. The implantable medical device of claim 24, wherein the processor is configured to generate the version of the second machine learning model by being further configured to train the second machine learning model on the second dataset.

26. The implantable medical device of claim 25, wherein the processor is configured to train the second machine learning model on the second dataset by being further configured to:
extract features from a plurality of physiological records included in the second dataset; and
train the second machine learning model on the extracted features.

27. The implantable medical device of claim 26, wherein each of the plurality of physiological records is of a same type.

28. The implantable medical device of claim 27, wherein the same type comprises any one of:
electrical activity of a brain, neural tissue motion, heart rate, blood profusion, blood oxygenation, neurotransmitter concentrations, blood glucose, sweat hormones, body motion, and pH level.

29. The implantable medical device of claim 24, wherein the processor is further configured to transmit the version of the second machine learning model to the server through the interface.

\* \* \* \* \*